(12) United States Patent
Campton et al.

(10) Patent No.: US 9,128,017 B2
(45) Date of Patent: Sep. 8, 2015

(54) DEVICE, SYSTEMS AND METHODS FOR ANALYZING A TARGET ANALYTE

(71) Applicant: RareCyte, Inc., Seattle, WA (US)

(72) Inventors: Daniel Campton, Seattle, WA (US); Jackie Lynn Stilwell, Sammamish, WA (US); Arturo Ramirez, Seattle, WA (US); Jennifer Chow, Seattle, WA (US)

(73) Assignee: RARECYTE, INC., Seattle, WA (US)

( * ) Notice: Subject to any disclaimer, the term of this patent is extended or adjusted under 35 U.S.C. 154(b) by 46 days.

(21) Appl. No.: 14/213,751

(22) Filed: Mar. 14, 2014

(65) Prior Publication Data

US 2014/0287487 A1  Sep. 25, 2014

Related U.S. Application Data

(60) Provisional application No. 61/803,340, filed on Mar. 19, 2013.

(51) Int. Cl.
| | |
|---|---|
| *B01L 99/00* | (2010.01) |
| *G01N 1/40* | (2006.01) |
| *G01N 1/28* | (2006.01) |
| *G01N 33/49* | (2006.01) |
| *B01L 3/00* | (2006.01) |

(52) U.S. Cl.
CPC .......... *G01N 1/4077* (2013.01); *B01L 3/50825* (2013.01); *G01N 1/28* (2013.01); *G01N 33/49* (2013.01); *B01L 3/50215* (2013.01); *B01L 2200/0668* (2013.01); *B01L 2300/042* (2013.01); *B01L 2300/046* (2013.01); *B01L 2300/047* (2013.01); *B01L 2400/043* (2013.01); *G01N 2001/4083* (2013.01)

(58) Field of Classification Search
CPC ................... B01L 2300/042; B01L 2300/047; B01L 2400/043; B01L 3/50215; B01L 3/50825; B01L 3/5021; G01N 2001/4083
See application file for complete search history.

(56) References Cited

U.S. PATENT DOCUMENTS

| | | | | |
|---|---|---|---|---|
| 3,888,113 | A | * | 6/1975 | Miranda ...................... 73/64.41 |
| 4,769,130 | A | | 9/1988 | Christensen |
| 5,736,033 | A | | 4/1998 | Coleman et al. |
| 6,549,794 | B1 | | 4/2003 | Nadeau, Jr. et al. |
| 2006/0021673 | A1 | * | 2/2006 | Rodewald ...................... 141/127 |
| 2011/0097816 | A1 | | 4/2011 | Goodwin |

FOREIGN PATENT DOCUMENTS

WO            92/04961 A1    4/1992

\* cited by examiner

*Primary Examiner* — Paul Hyun

(74) *Attorney, Agent, or Firm* — Olympic Patent Works PLLC

(57) ABSTRACT

This disclosure is directed to a cap for obtaining a target analyte from a suspension. The cap introduces a magnetic field or a magnetic gradient to the tube to draw the target analyte bound to a particle to the cap. In one aspect, a cap includes a magnetic insert and a receiving piece. The magnetic insert includes a stopper and a magnet extending from the stopper; and, the receiving piece, which is configured to hold the magnetic insert, includes a receiving stopper and a sheath. The sheath may include imaging slides on opposite sides of the sheath. In another aspect, the cap may include a stopper and an embedded magnet. The cap may include an analysis piece on a bottom end of the stopper. In yet another aspect, the cap may include a fluid compartment and a filter at a bottom end of the stopper.

21 Claims, 22 Drawing Sheets

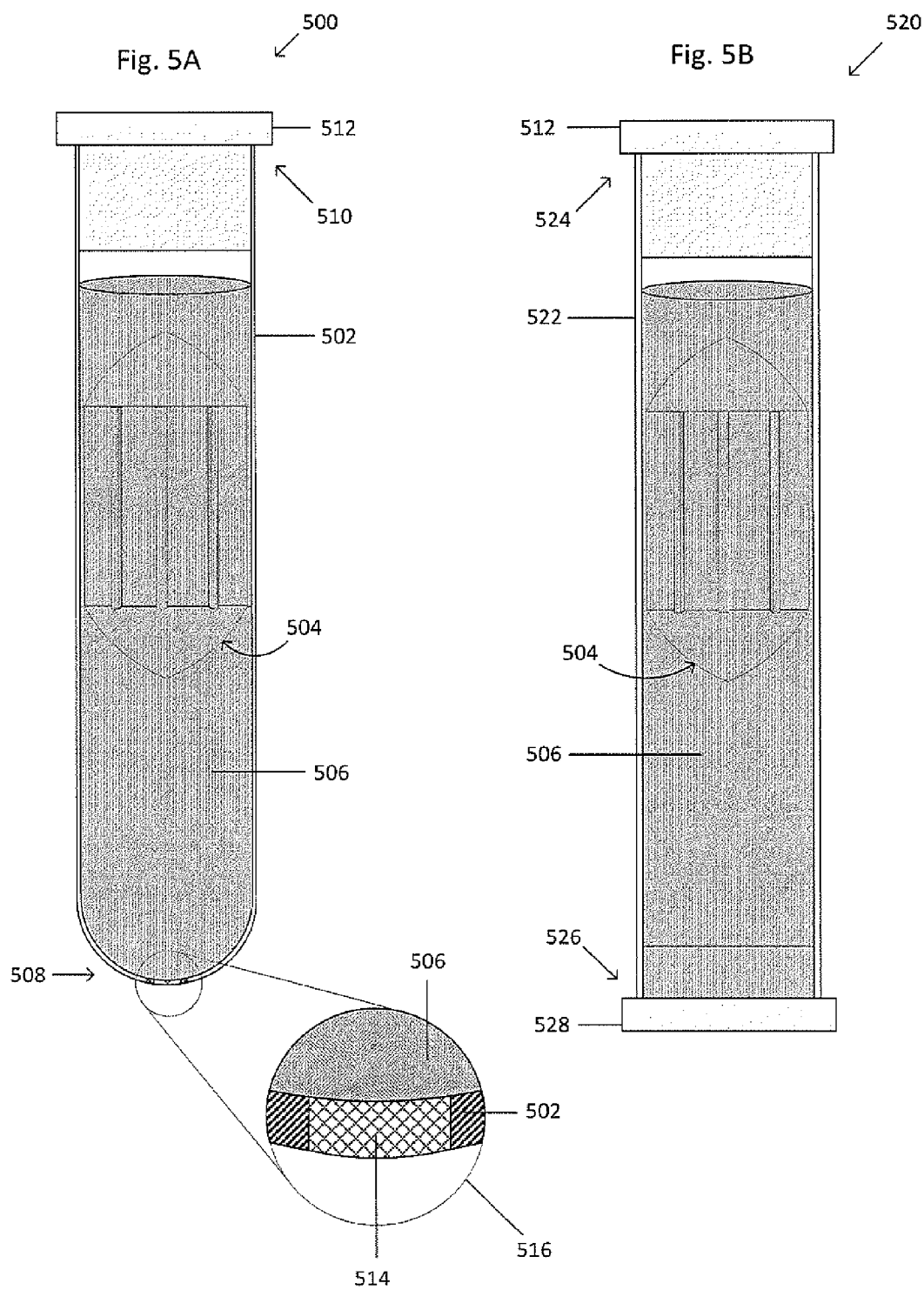

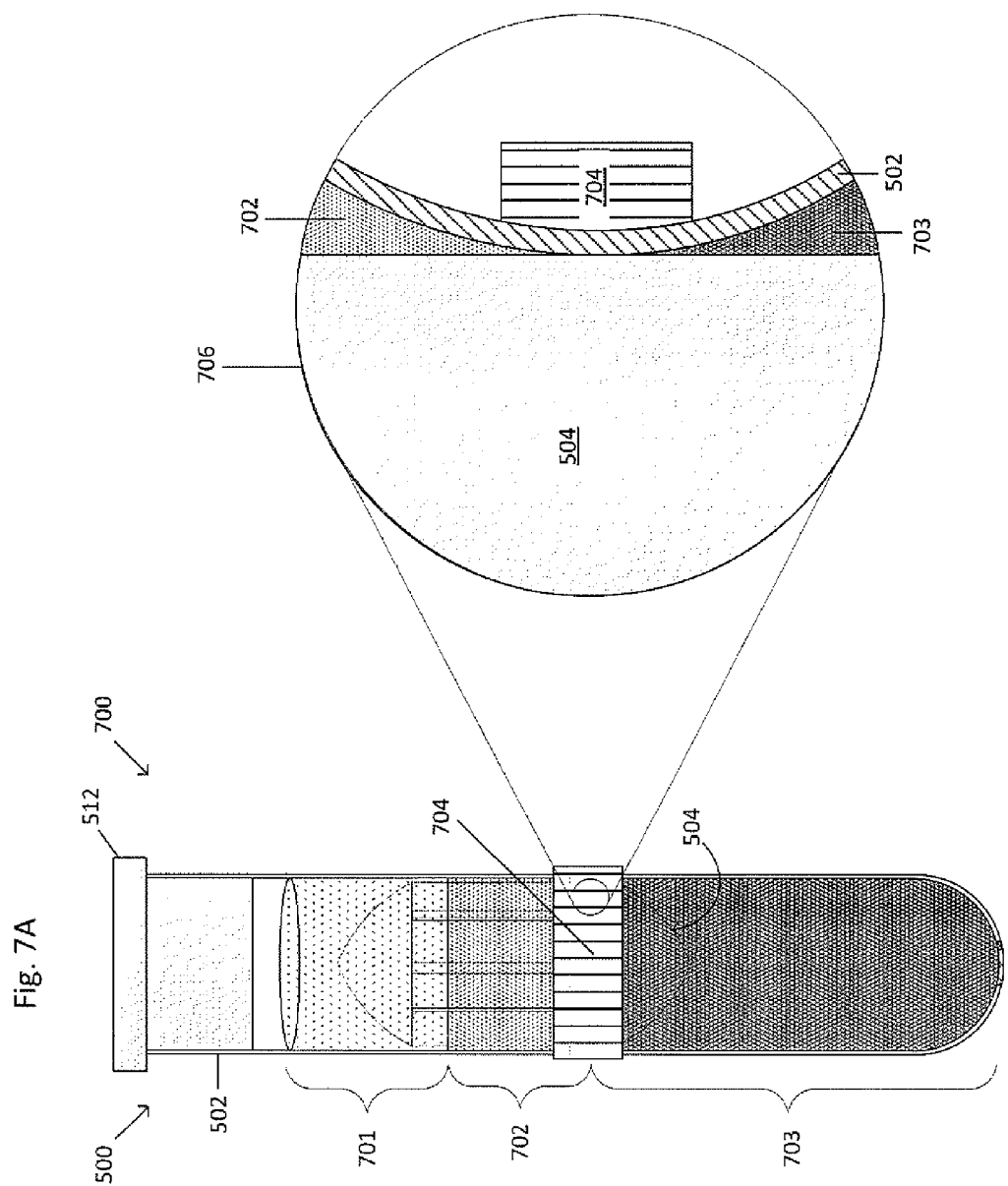

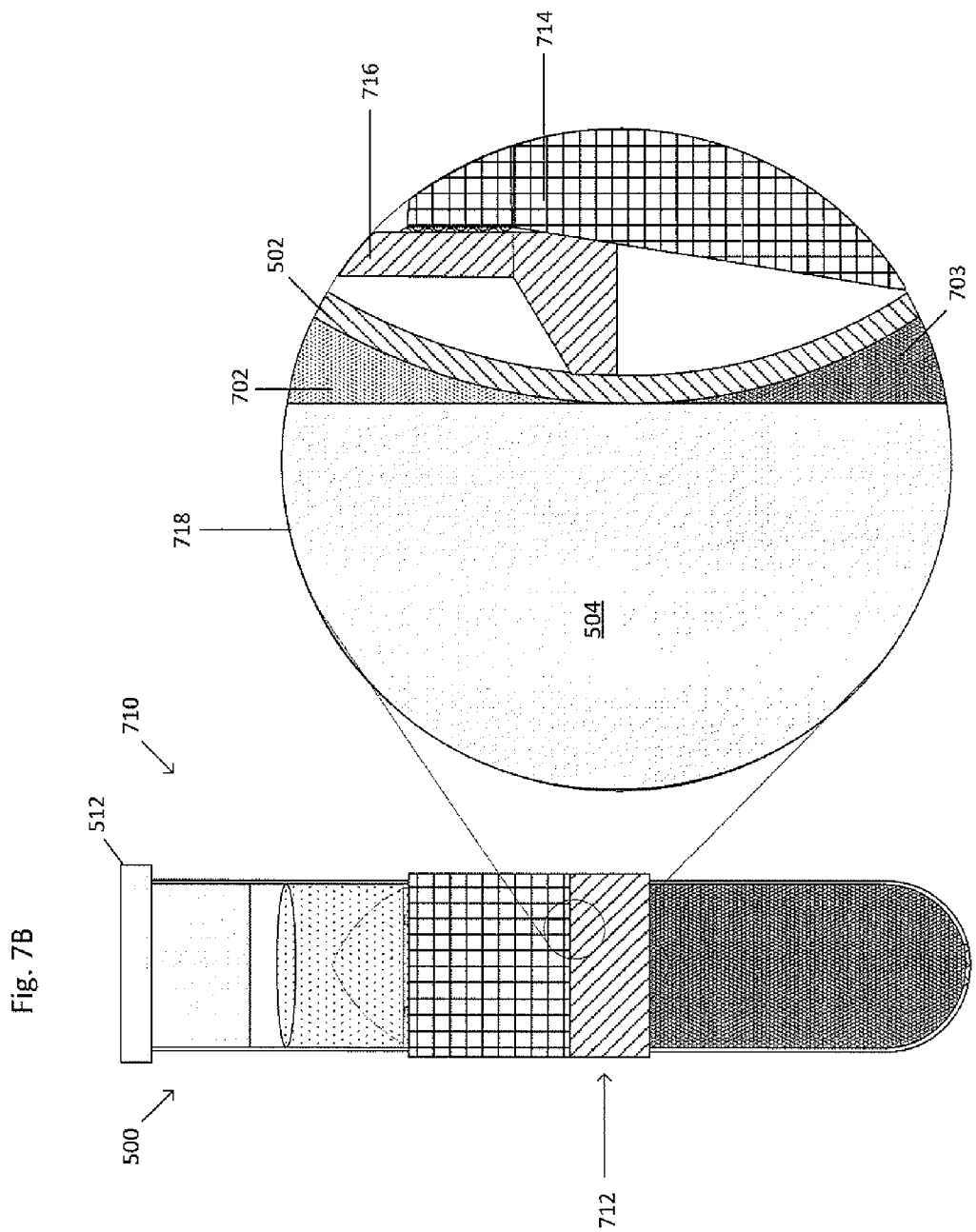

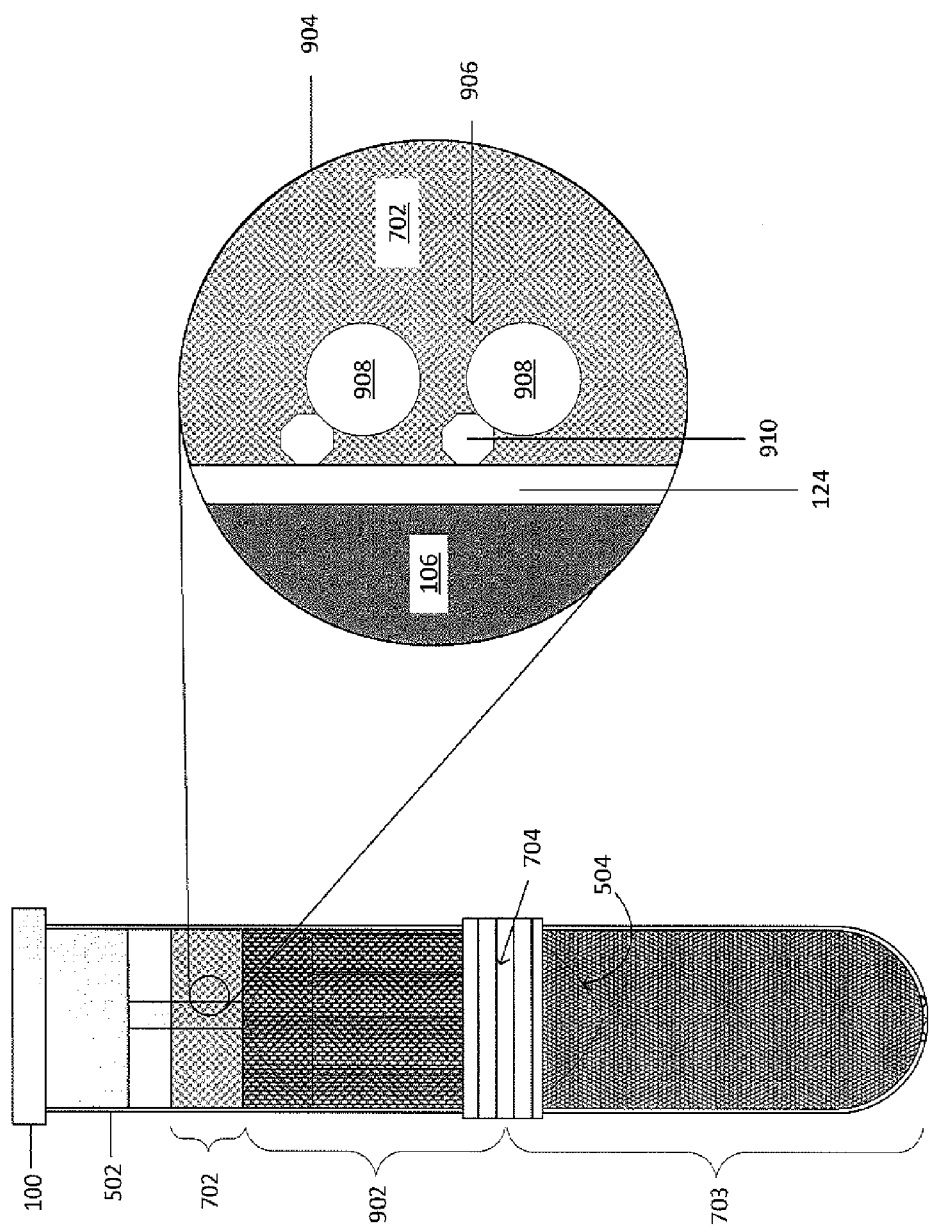

DEVICE, SYSTEMS AND METHODS FOR ANALYZING A TARGET ANALYTE

CROSS-REFERENCE TO A RELATED APPLICATION

This application claims the benefit of Provisional Application No. 61/803,340, filed Mar. 19, 2013.

TECHNICAL FIELD

This disclosure relates generally to density-based fluid separation and, in particular, to systems and methods the separation, axial expansion of constituent suspension fractions layered by centrifugation, and analysis of a target analyte.

BACKGROUND

Suspensions often include materials of interest that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as fetal cells, endothelial cells, epithelial cells, parasites, bacteria, and inflammatory cells, and viruses, including HIV, cytomegalovirus, hepatitis C virus, and Epstein-Barr virus and nucleic acids. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field microscopy.

On the other hand, materials of interest composed of particles that occur in very low numbers are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers, but CTCs occur in very low numbers in peripheral whole blood samples. For instance, a 7.5 ml sample of peripheral whole blood that contains as few as 3 CTCs is considered clinically relevant in the diagnosis and treatment of a cancer patient. However, detecting even 1 CTC in a 7.5 ml blood sample may be clinically relevant and is equivalent to detecting 1 CTC in a background of about 40-50 billion red and white blood cells. Using existing techniques to find, isolate and extract as few as 3 CTCs of a whole blood sample is extremely time consuming, costly and is extremely difficult to accomplish.

As a result, practitioners, researchers, and those working with suspensions continue to seek systems and methods to more efficiently and accurately detect, isolate and extract target materials of a suspension.

DESCRIPTION OF THE DRAWINGS

FIGS. 5A-5B show isometric views of two example tube and float systems.
FIG. 7A shows an example clamp forming a seal between a float and a tube.
FIG. 7B shows an example clamp forming a seal between a float and a tube.
FIG. 9 shows an example system for separating a target analyte.

DETAILED DESCRIPTION

This disclosure is directed to systems and methods for analyzing a target analyte of a suspension. In one aspect, a system can be composed of a tube, a float, and a cap, the cap comprising a magnetic insert and a receiving piece. The system may also include a primary fluid to change the location of the target analyte within the tube. The magnetic insert includes a stopper and a magnet extending from the stopper; and, the receiving piece, which is configured to hold the magnetic insert, includes a receiving stopper and a sheath. The sheath may include imaging slides on opposite sides of the sheath. The cap introduces a magnetic field or a magnetic gradient to the tube to draw the target analyte bound to a particle to the cap. In another aspect, the cap may include a stopper and an embedded magnet. The cap may include an analysis piece on a bottom end of the stopper. In another aspect, the cap may include a fluid compartment and a filter at a bottom end of the stopper. The system, in another aspect, may include a separating fluid to separate non-target analytes from the target analyte.

Magnetic Cap

Figure 1A:
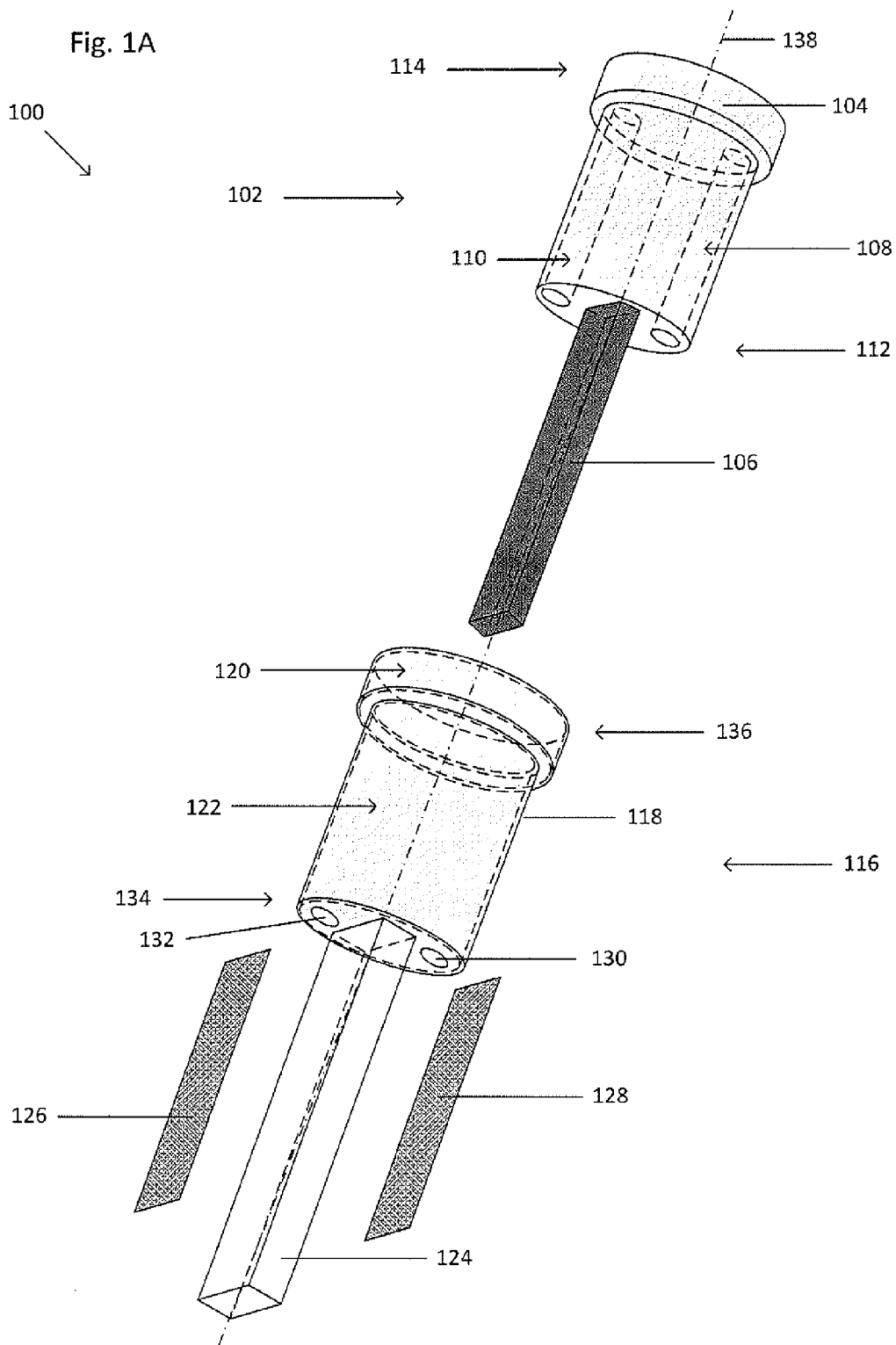
FIGS. 1A-1C show exploded views of example magnetic caps.

FIG. 1A shows an exploded view of an example magnetic cap 100. The magnetic cap 100 includes a magnetic insert 102 and a receiving piece 116, the receiving piece 116 configured to hold the magnetic insert 102, such that the magnetic insert 102 and the receiving piece 116 are coaxial along a central axis 138. The magnetic insert 102 includes a stopper 104 with a bottom end 112 and a top end 114. The magnetic insert 102 also includes a magnet 106, the magnet 106 extending outward from the bottom end 112 of the stopper 104. The magnet 106 may be a permanent magnet, such as a bar magnet or any other appropriately-shaped magnet. The magnetic insert 102 may also include an inlet port 108 and an outlet port 110. The inlet port 108 and the outlet port 110 may, individually, extend the full length of the stopper 104 or may extend only a partial length of the stopper 104. The inlet port 108 permits fluids to be introduced into the system through the magnetic cap 100 without having to remove the magnetic cap 100 from a vessel or without having to puncture the magnetic cap 100. The outlet port 110 permits fluids to be removed from the system through the magnetic cap 100 without having to remove the magnetic cap 100 from the vessel or without having to puncture the magnetic cap 100. Alternatively, the magnetic cap 100 may include only a single port that permits fluids to be both introduced to and removed from the vessel.

The receiving piece 116 includes a receiving stopper 118 with a bottom end 134 and a top end 136. The bottom end 134 is sized and shaped to fit within the vessel opening; the top end 136 may be sized and shaped to prevent the receiving piece 116 from sliding further into the vessel, such as by being greater in diameter (i.e. wider) than a diameter of an inner wall of the vessel opening. The receiving piece 116 also includes a sheath 124 that extends outward from the bottom end 134 of the receiving stopper 118. The sheath 124 is hollow and is configured to receive the magnet 106 of the magnetic insert 102. The sheath 124 may be rectangular, hemispherical, triangular, conical, polyhedral, or any appropriate shape. The receiving stopper 118 includes an opening 122 configured to receive the bottom end 112 of the stopper 104 and a cavity 120 configured to receive the top end 114 of the stopper 104. The receiving piece 116 may include an inlet opening 130 and an outlet opening 132 at the bottom end 134. The inlet opening 130 and the outlet opening 132 correspond to the inlet port 108 and the outlet port 110, respectively, of the magnetic insert 102, to permit fluids to flow into and out of the vessel without being trapped within the receiving stopper 118.

The receiving piece 116 may include imaging slides 126 and 128 located on opposite sides of the sheath 124. The imagining slides 126 and 128 are smooth, thin, flat pieces of material that may be removably attached to the sheath 124 by an adhesive, an oil, a gel, a grease, such as vacuum grease, a vacuum, or the like. The imaging slides 126 and 128 may be reflective, opaque, transparent or translucent. The imaging slides 126 and 128 may be composed of glass, plastic, metal, or combinations thereof. For example, the imaging slides 126 and 128 can be a thin microscope slide disposed so that the imaging slides 126 and 128 may be detached from the sheath 124 and placed onto a fluorescent microscope to image for a target analyte. The imaging slides 126 and 128 may be affixed to a frame or holder to facilitate ease of handling.

The magnetic cap 100 may be used to analyze a target analyte of a suspension. The target analyte, having been conjugated with a particle to form a target analyte-particle complex, may be attracted to and held to one of the imaging slides 126 and 128 by a magnetic field or a magnetic gradient created by the magnet 106. The magnetic cap 100 may then be removed from the vessel in which the magnetic cap 100 was placed. The imaging slides 126 and 128, with target analyte-particle complex held to the surface of the imaging slides 126 and 128, may be removed from the sheath 126, and placed onto or within an imaging device, such as a fluorescent microscope, to detect or analyze the target analyte.

The particle may come in any form, including, but not limited to, a bead, a nanoparticle (such as a quantum dot), a shaving, a filing, or the like, such that the particle is capable of being attracted by a magnetic field or magnetic gradient introduced by a magnet. The particle may itself be magnetic, diamagnetic, ferromagnetic, or paramagnetic.

Figure 1B:
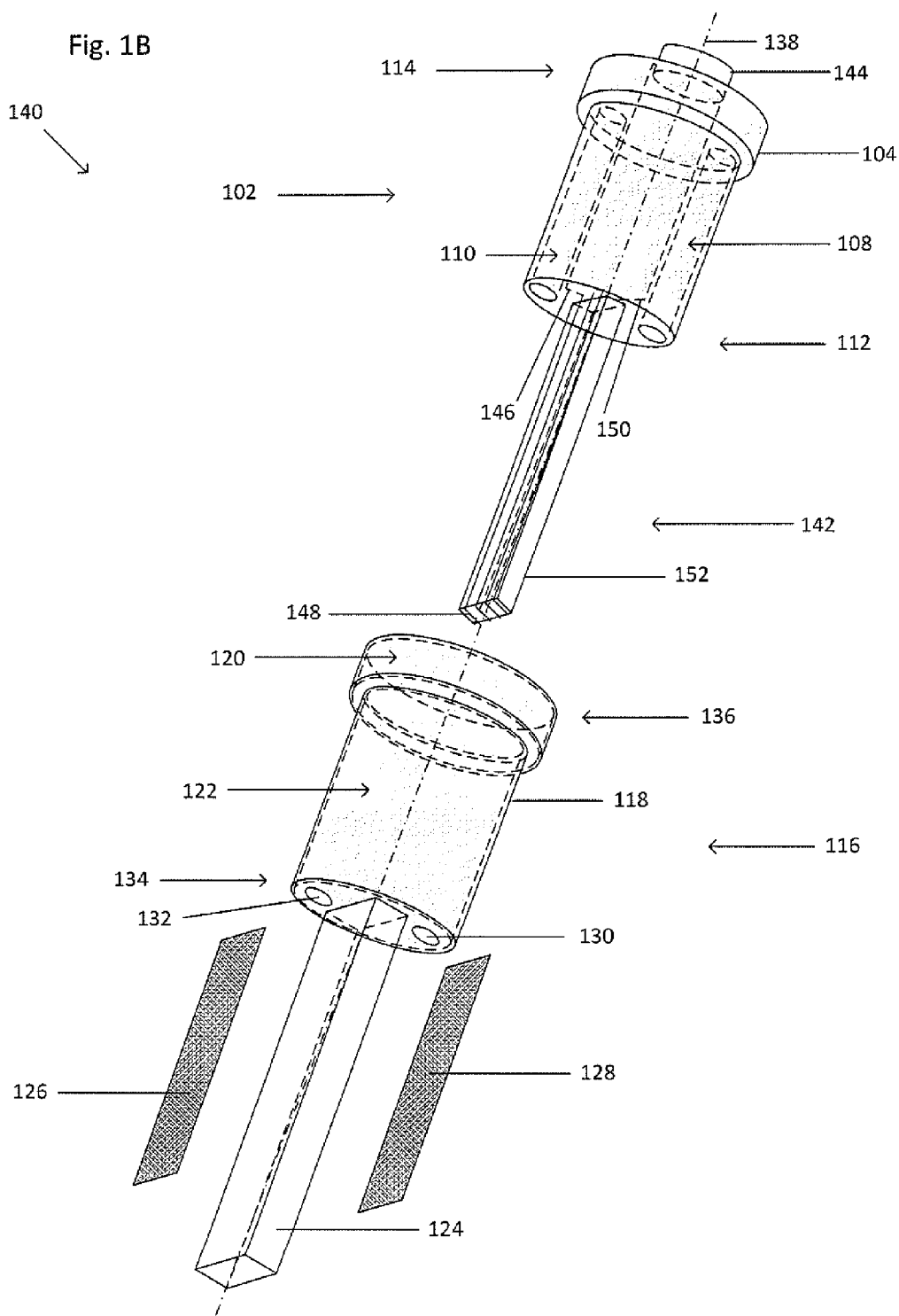

FIG. 1B shows an exploded view of an example magnetic cap 140. The magnetic cap 140 is similar to the magnetic cap 100, except that the magnetic cap 140 includes an electromagnet 142 instead of the magnet 106. The electromagnet 142 includes a power source 144, such as a battery, DC or AC current supply, external to, disposed on or within the top end 114 of the stopper 104, a first lead 146, a coil 148, a second lead 150, and a core 152 around which the coil 148 is wrapped. The magnetic cap 140 may also include a switch or control mechanism.

Figure 1C:
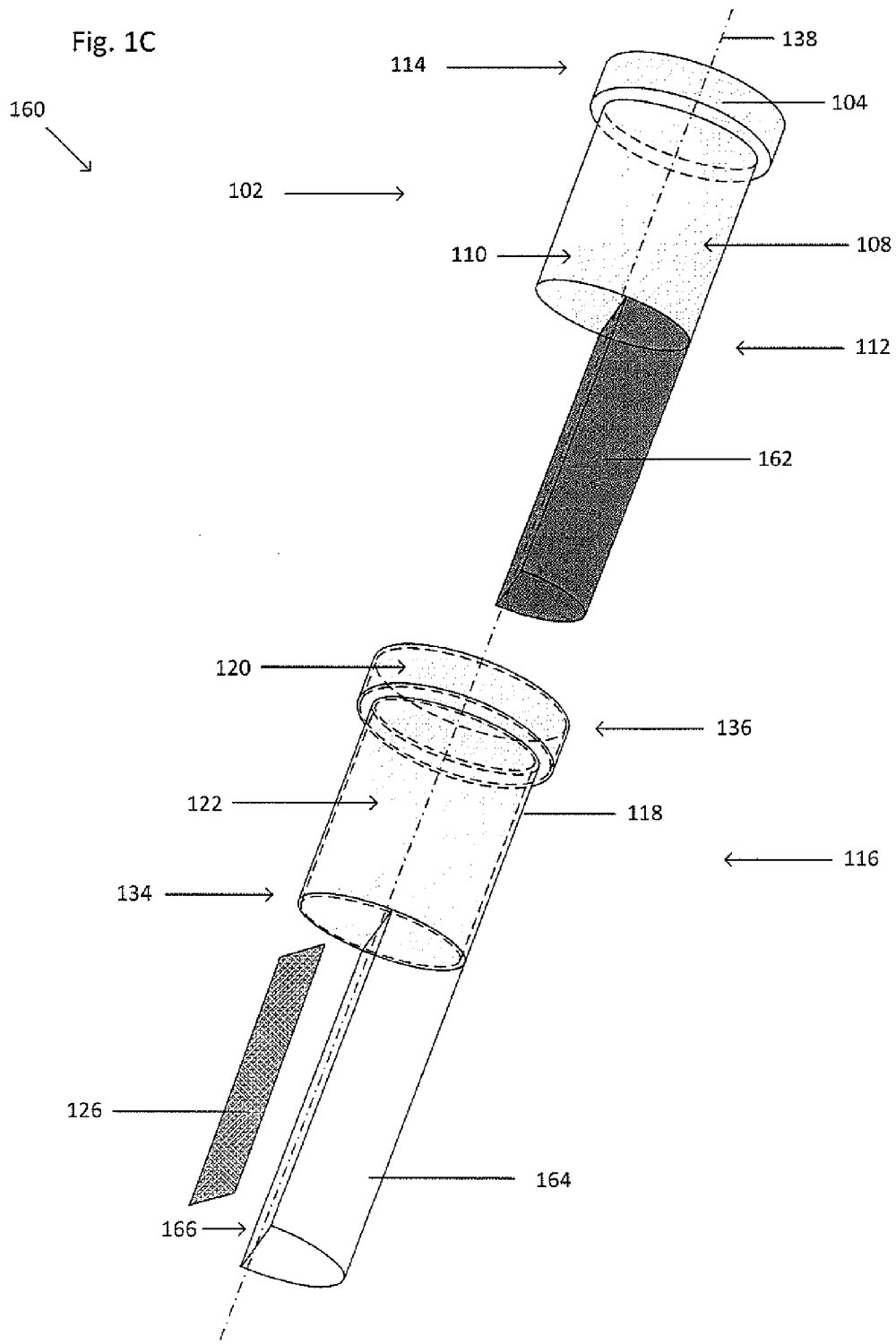

FIG. 1C shows an exploded view of an example magnetic cap 160. The magnetic cap 160 is similar to the magnetic cap 100, except that the magnetic cap 160 includes a sheath 164 that is sized and shaped to fit flush against the sidewall of the vessel, such as a tube, thereby preventing any fluids from flowing between the sheath 164 and the sidewall of the vessel. The sheath 164 may be rectangular, hemispherical, triangular, conical, polyhedral, or any appropriate shape. The sheath 164 includes a flat facet 166 to hold the imaging slide 126 within a sample contained by the vessel. A magnet 162 may be shaped the same as the sheath 162 and sized proportionally to fit within the sheath 164. Alternatively, the magnet 162 may be any magnet capable of fitting within the sheath 164.

Figure 2:
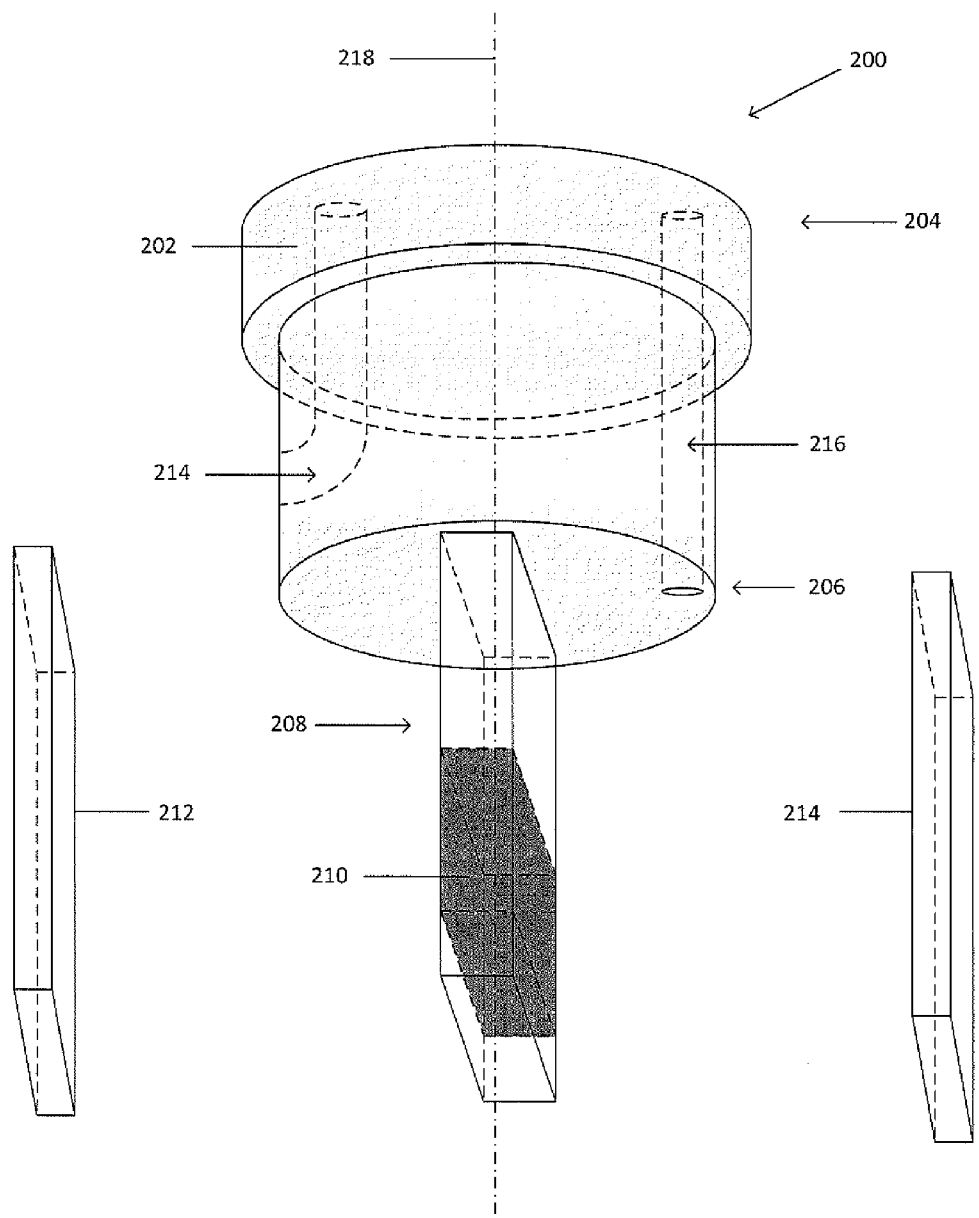
FIG. 2 shows an exploded view of an example magnetic cap.

FIG. 2 shows an exploded view of an example magnetic cap 200. The magnetic cap 200 includes a stopper 202 with a bottom end 206 and a top end 204. The magnetic cap 200 also includes a shaft 208, the shaft 208 extending outward from the bottom end 206 of the stopper 202. The magnetic cap 200 further includes a magnet 210 embedded within the shaft 208. The magnet 210 may be a permanent magnet, such as a bar magnet or any other appropriately-shaped magnet. The magnetic cap 200 may also include an inlet port 214 and an outlet port 216 similar to the inlet and outlet ports 108 and 110 as shown in FIG. 1A. It should be noted that inlet port 214 is shown in FIG. 2 as extending only a partial length of the stopper 202 and exiting at a sidewall of the stopper 202. The magnetic cap 200 also includes imaging slides 212 and 214 located on opposite sides of the shaft 208. The imaging slides 212 and 214 are similar to the imaging slides 126 and 128 as shown in FIG. 1A.

Alternatively, the shaft 208 may be sized and shaped to fit flush against the sidewall of the vessel, such as a tube, thereby preventing any fluids from flowing between the shaft 208 and the sidewall of the vessel. The shaft 208 may be rectangular, hemispherical, triangular, conical, polyhedral, or any appropriate shape. The shaft may include a flat facet to hold an imaging slide within a sample contained by the vessel. The magnet 210 may be shaped the same as the shaft 208 and sized proportionally to be embedded within the shaft 208; or, the magnet 210 may be any magnet capable of embedding within the shaft 208.

Figure 3A:
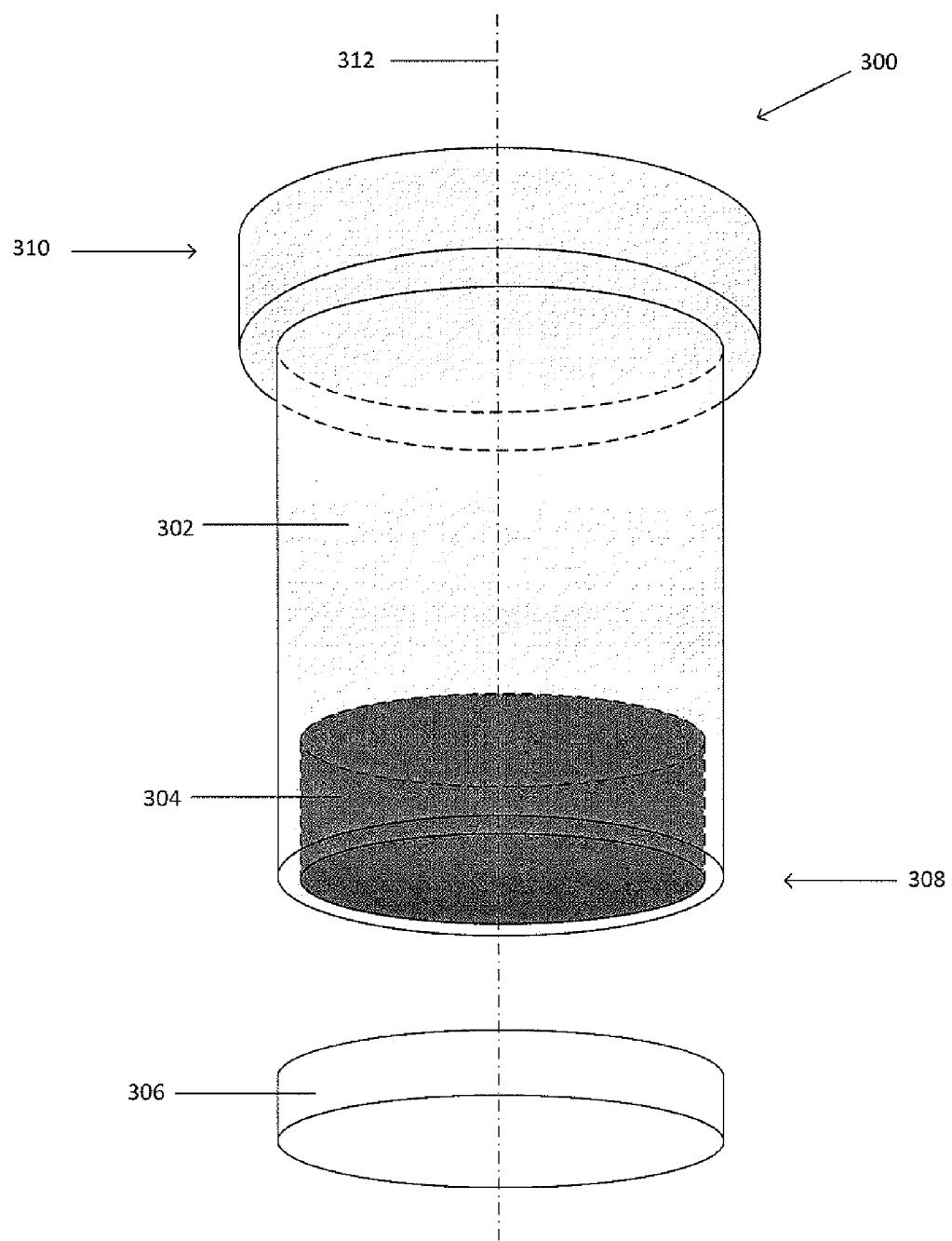
FIGS. 3A-3E show example magnetic caps.
Figure 3B:
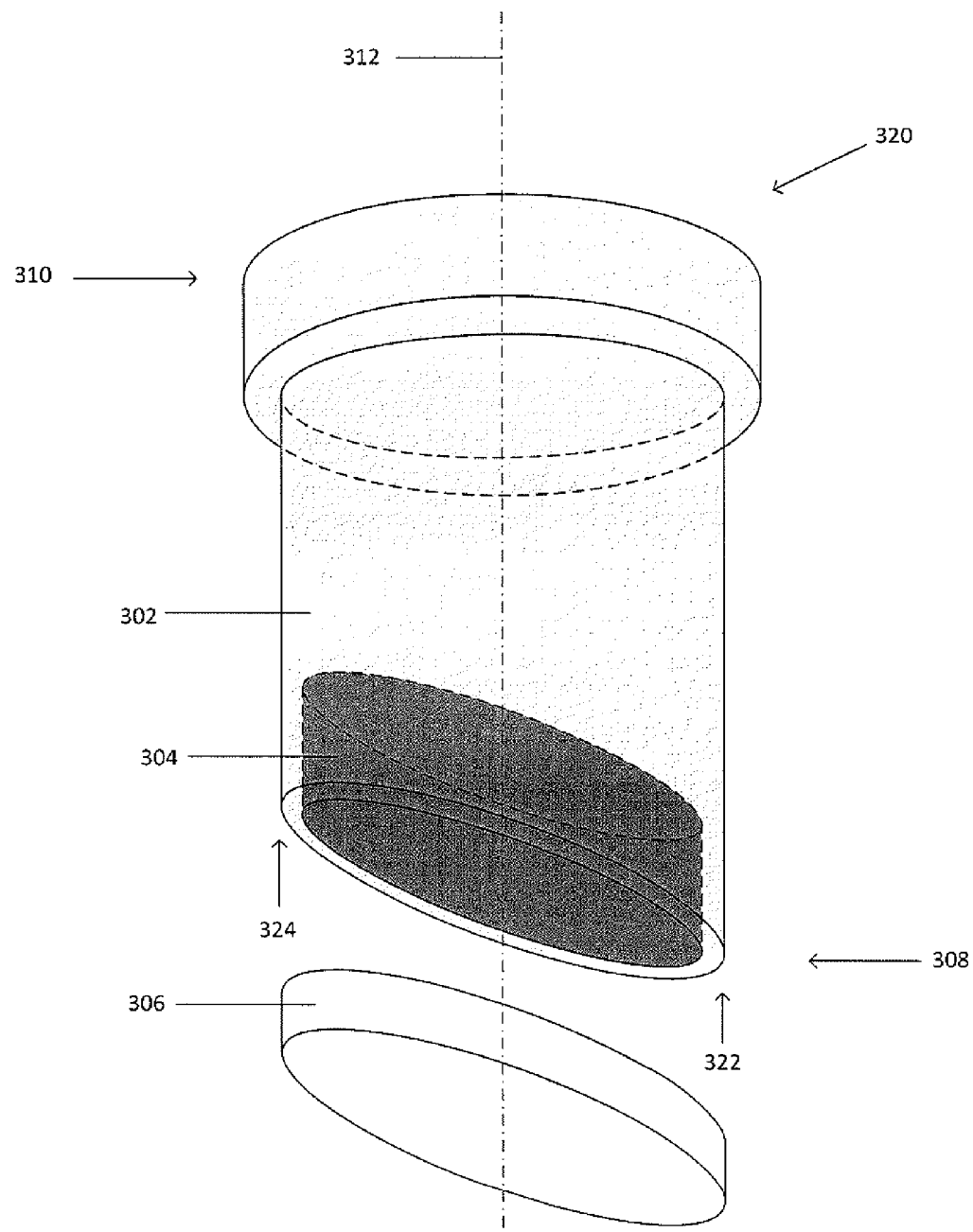

FIG. 3A shows an exploded view of an example magnetic cap 300. The magnetic cap 300 includes a stopper 302 with a bottom end 308 and a top end 310. The bottom end 308 is sized and shaped to fit within an opening of a vessel. The top end 310 may be sized and shaped to prevent the magnetic cap 300 from sliding further into the vessel, such as by being greater in diameter (i.e. wider) than a diameter of an inner wall of the vessel. The magnetic cap 300 also includes a cap magnet 304. The cap magnet 304 may be embedded within the stopper 302 or may be attached to the bottom end 308 of the stopper 302 with an adhesive, an oil, a gel, a grease, or the like. The magnetic cap 300 may also include an analysis piece 306, the analysis piece 306 being removably attached to the bottom end 308 of the stopper 302 or to the cap magnet 304 via an adhesive, an oil, a gel, a grease, such as vacuum grease, a vacuum, or the like. The analysis piece 306 is a smooth, thin, flat piece of material that may be removed from the stopper 302 or the cap magnet 304. The analysis piece 306 may be reflective, opaque, transparent or translucent. The analysis piece 306 may be composed of glass, plastic, metal, or combinations thereof. For example, the analysis piece 306 can be a thin microscope slide disposed so that the analysis piece 306 may be detached from the stopper 302 and placed onto a fluorescent microscope to image for a target analyte. The bottom end 308 of the magnetic cap 300 may be perpendicular with respect to a central axis 312 of the magnetic cap 300, as shown in FIG. 3A; or, the bottom end 308 may be angled with respect to the central axis 312 of the magnetic cap 320, as shown in FIG. 3B, such that a first edge 322 of the bottom end 308 is longer than a second edge 324 of the bottom end 308. The angled bottom end 308 may decrease or inhibit the formation or presence of air bubbles on the analysis piece 306.

Figure 3C:
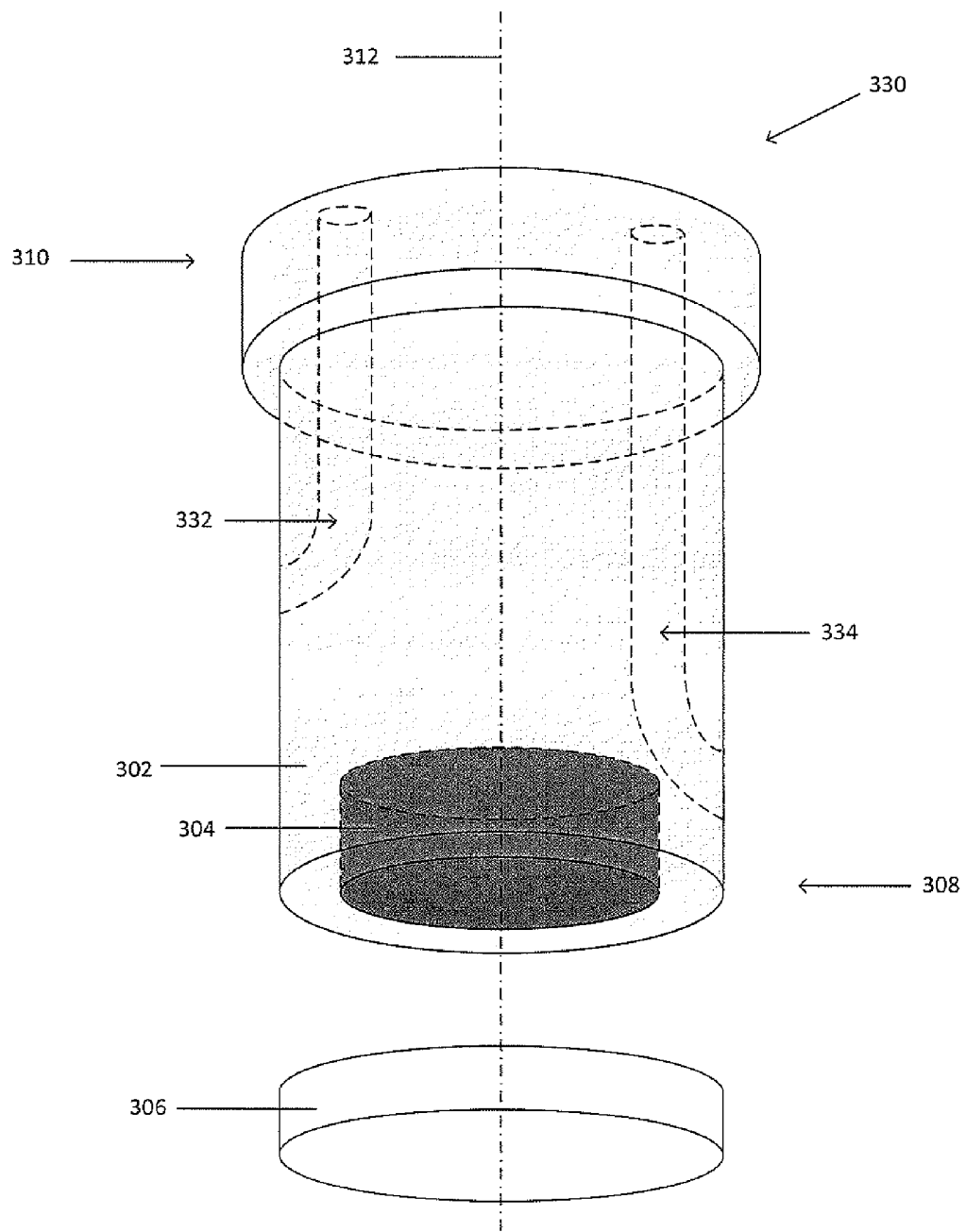

FIG. 3C shows an exploded view of an example magnetic cap 330. The magnetic cap 330 is similar to magnetic cap 300 except that magnetic cap 330 includes an inlet port 332 and an outlet port 334. The inlet port 332 and the outlet port 334 are similar to the inlet and outlet ports 214 and 216 as shown in FIG. 2.

Figure 3D:
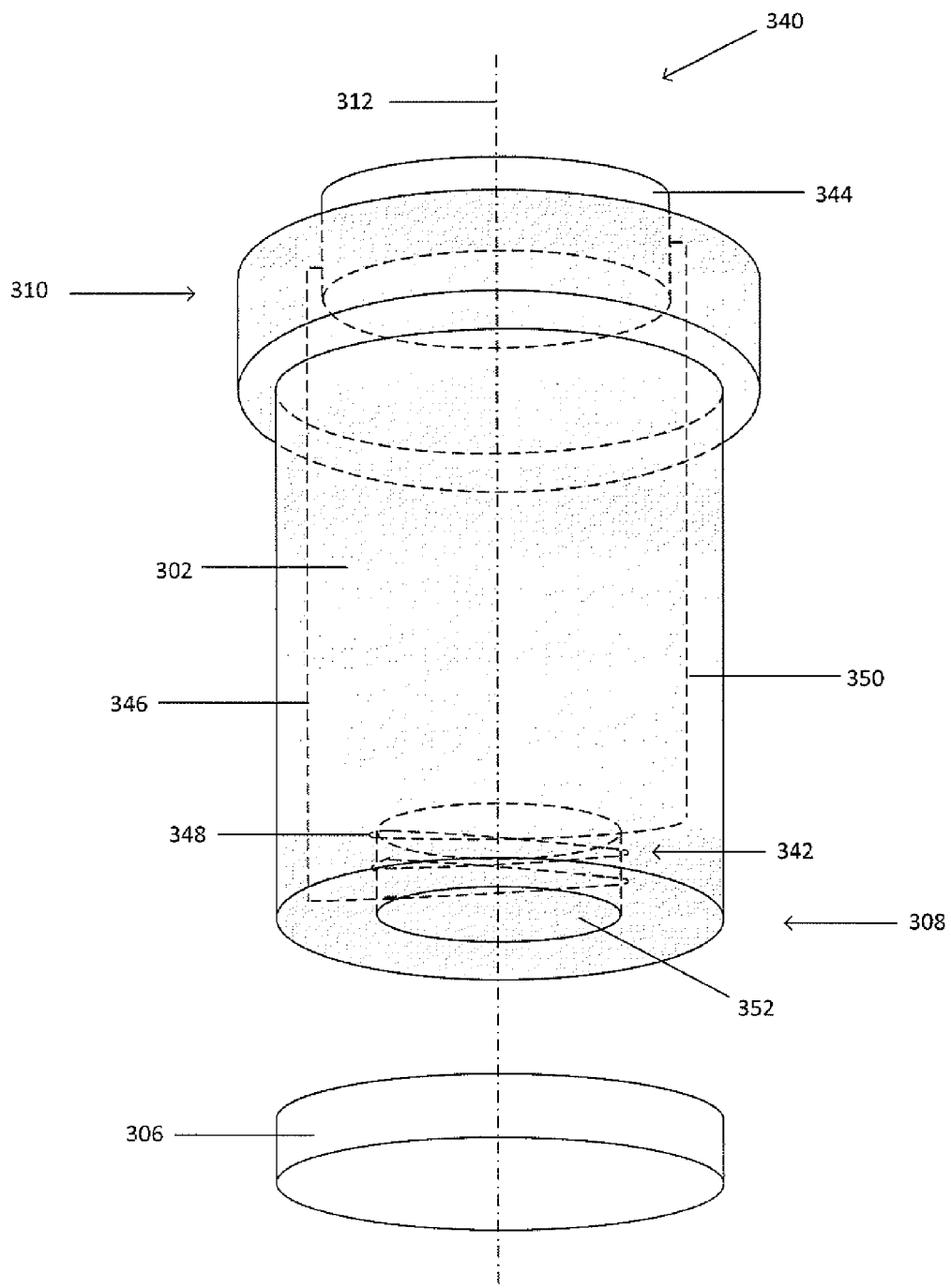

FIG. 3D shows an exploded view of an example magnetic cap 340. The magnetic cap 340 is similar to the magnetic cap 300, except that the magnetic cap 340 includes an electromagnet 342 instead of the magnet 306. The electromagnet 342 includes a power supply 344, such as a battery, DC or AC current supply, external to disposed on or within the top end 310 of the stopper 302, a first lead 346, a coil 348, a second lead 350, and a core 352 around which the coil 348 is wrapped. The magnetic cap 340 may also include a switch or control mechanism.

Figure 3E:
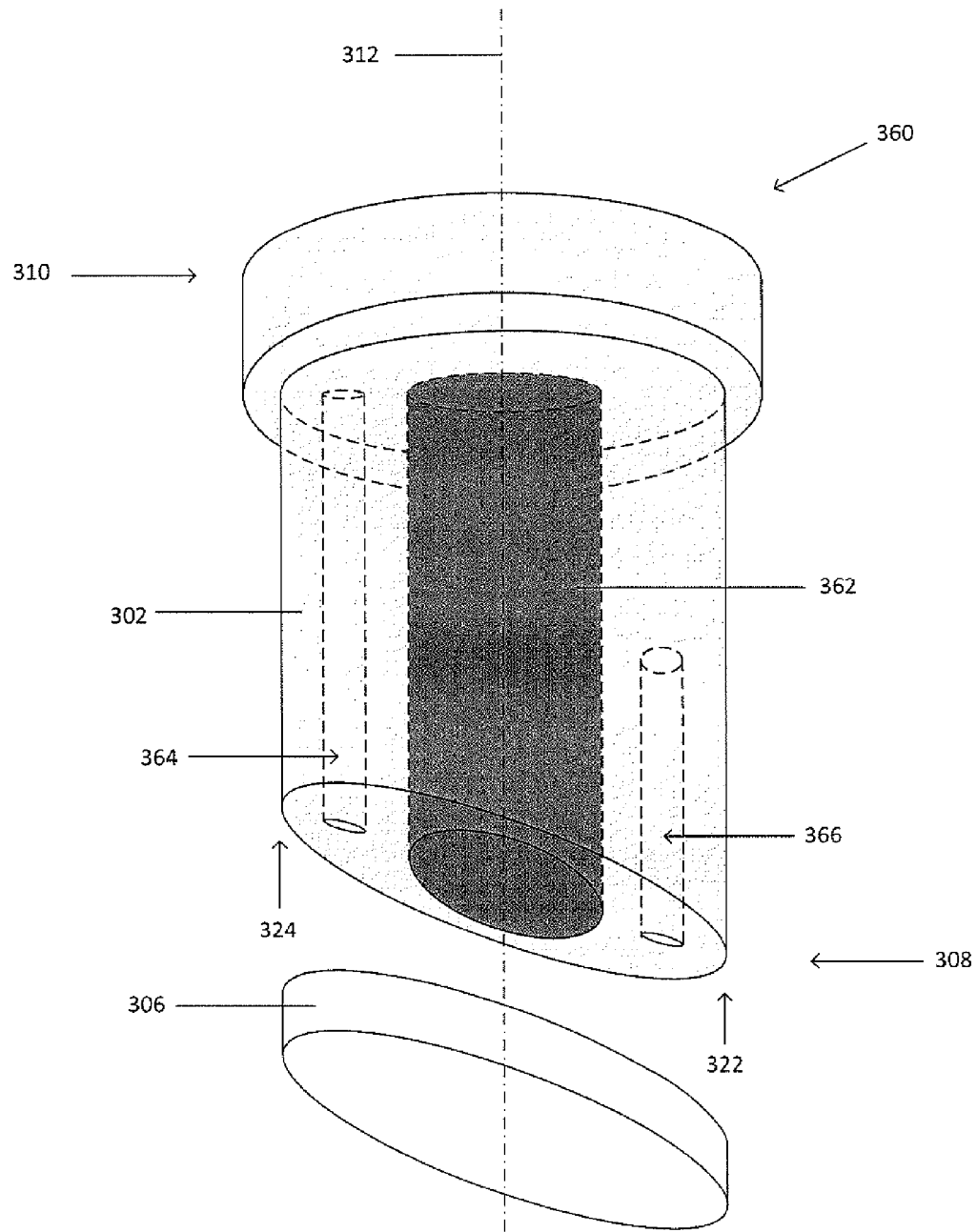

FIG. 3E shows an exploded view of an example magnetic cap 360. The magnetic cap 360 is similar to the magnetic cap 3B, except that the magnetic cap 360 includes an inlet/outlet port 364 to add or remove fluids and an ejection port 366 to accept an ejection prong (not shown to eject the analysis piece 306 from the bottom end 308 of the stopper 302. The ejection port 366 may extend from the top end 310 to the bottom end 308 of the stopper 302; or, the ejection port 366 may partially extend through the stopper 302, thereby extending from a sidewall of the stopper 302 to the bottom end 308 of the stopper 302. The magnetic cap 360 also includes a magnet 362.

Figure 4A:
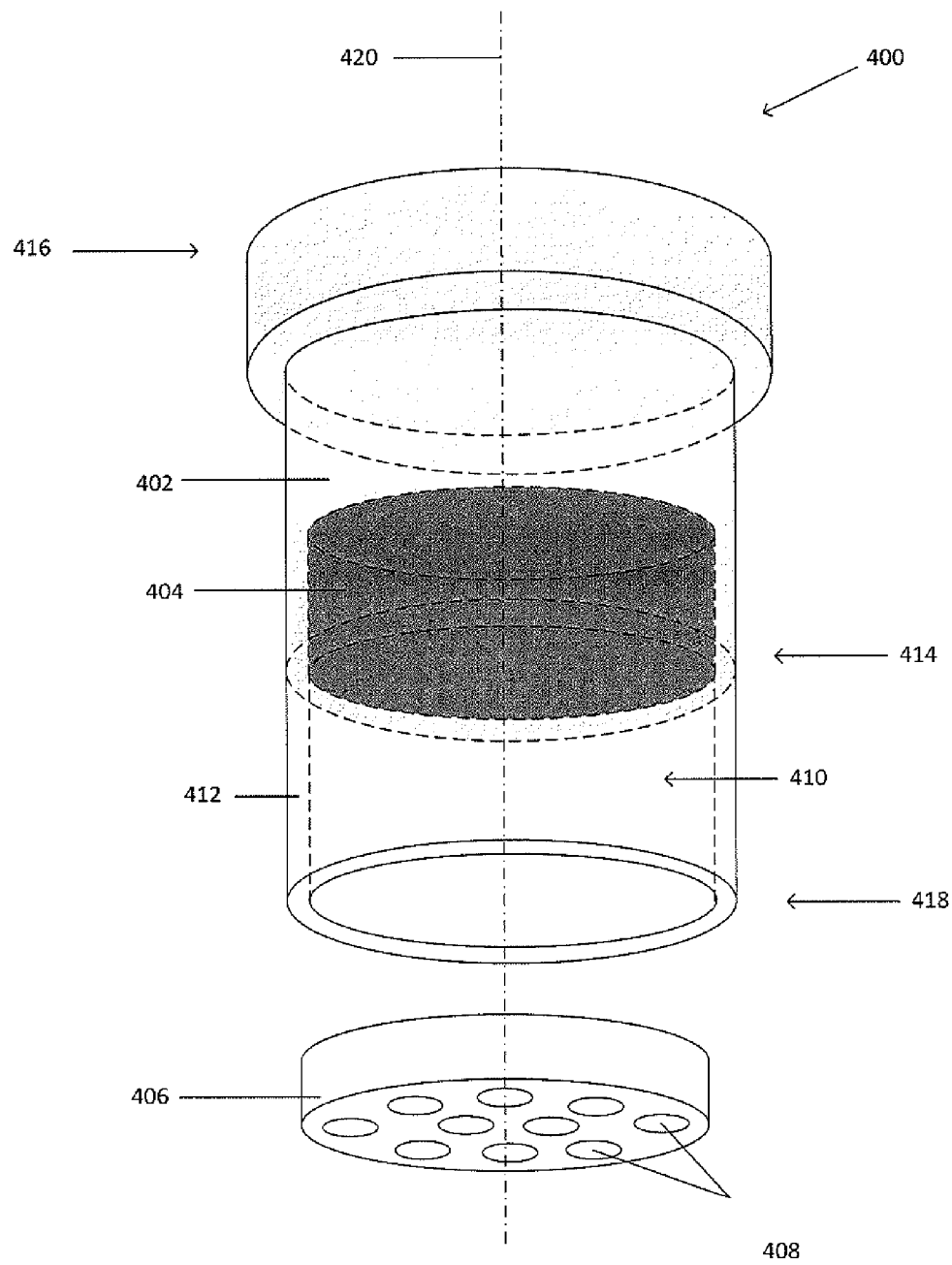
FIGS. 4A-4C show example magnetic caps.

FIG. 4A shows an exploded view of an example magnetic cap 400. The cap 400 includes a stopper 402 with a bottom end 414 and a top end 416. The bottom end 414 is sized and shaped to fit within an opening of a vessel. The top end 416 may be sized and shaped to prevent the magnetic cap 400 from sliding further into the vessel, such as by being greater in diameter (i.e. wider) than a diameter of an inner wall of the vessel. The cap 400 also includes a cap magnet 404, a fluid compartment 410, and a filter 406. The cap magnet 404 may be embedded within the stopper 402. The filter 406 includes pores 408 that are sized to allow unbound particles (i.e. particles not conjugated to any component of the suspension) to pass through the filter 406 and into the fluid compartment 410. The fluid compartment 410 is a cavity—between the bottom end 414 of the stopper 402 and the filter 406—formed by extending a sidewall 412 from the bottom end 414 of the stopper 402.

The magnetic cap 400 may be used to analyze a target analyte of a suspension. The filter 406 may also be configured to trap or hold the target analyte. The target analyte may be trapped within one of the pores 408 or may be held to the surface of the filter 406. The magnetic cap 400 may then be removed from a vessel.

Figure 4B:
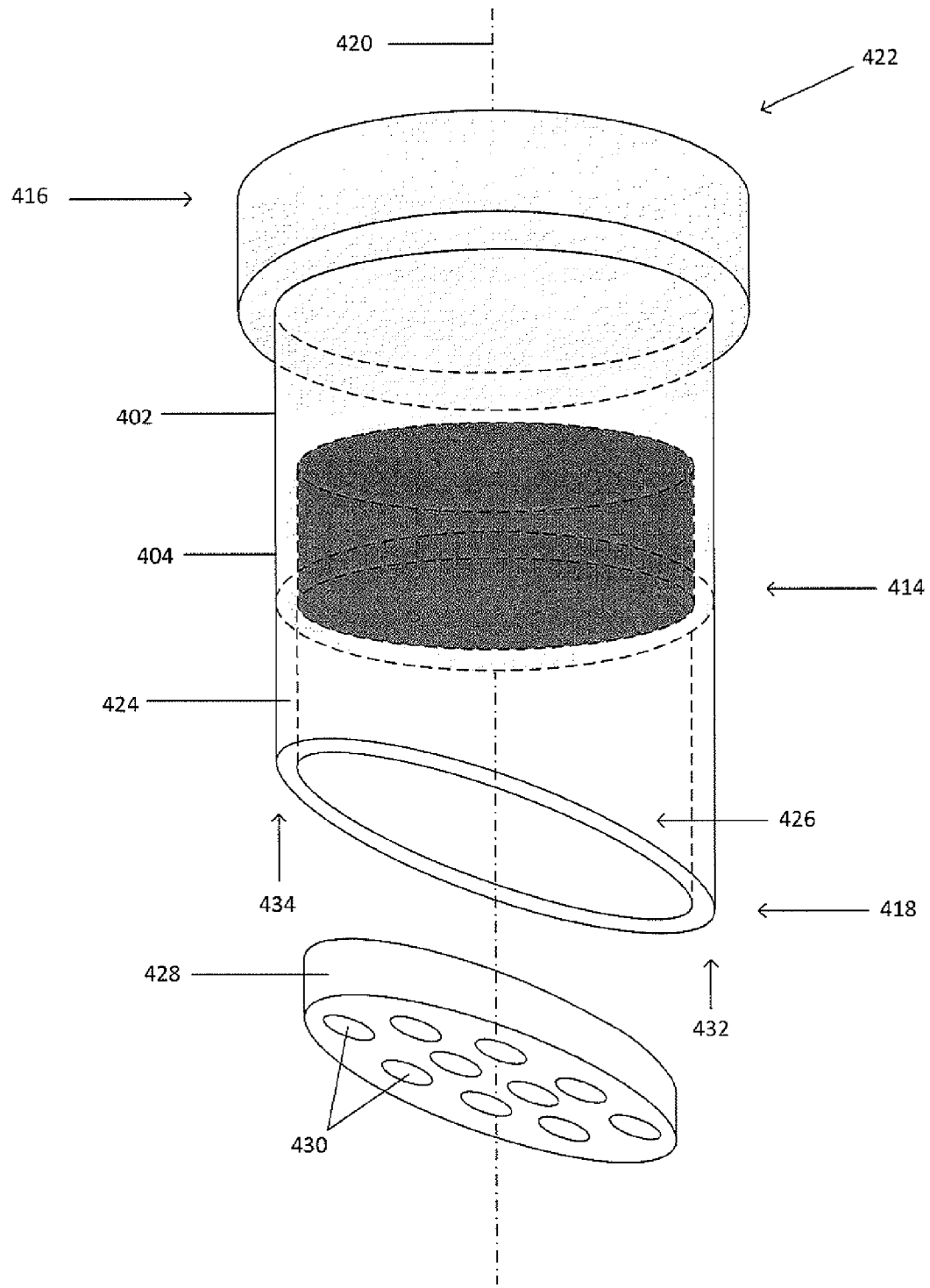

A filter end 418 of the magnetic cap 400 may be perpendicular with respect to a central axis 420 of the magnetic cap 400, as shown in FIG. 4A; or, the filter end 418 may be angled with respect to the central axis 420 of the magnetic cap 422, as shown in FIG. 4B, such that a first edge 432 of the filter end 418 is longer than a second edge 434 of the filter end 418. The angled filter end 418 may decrease or inhibit the formation or presence of air bubbles on the filter 428.

Figure 4C:
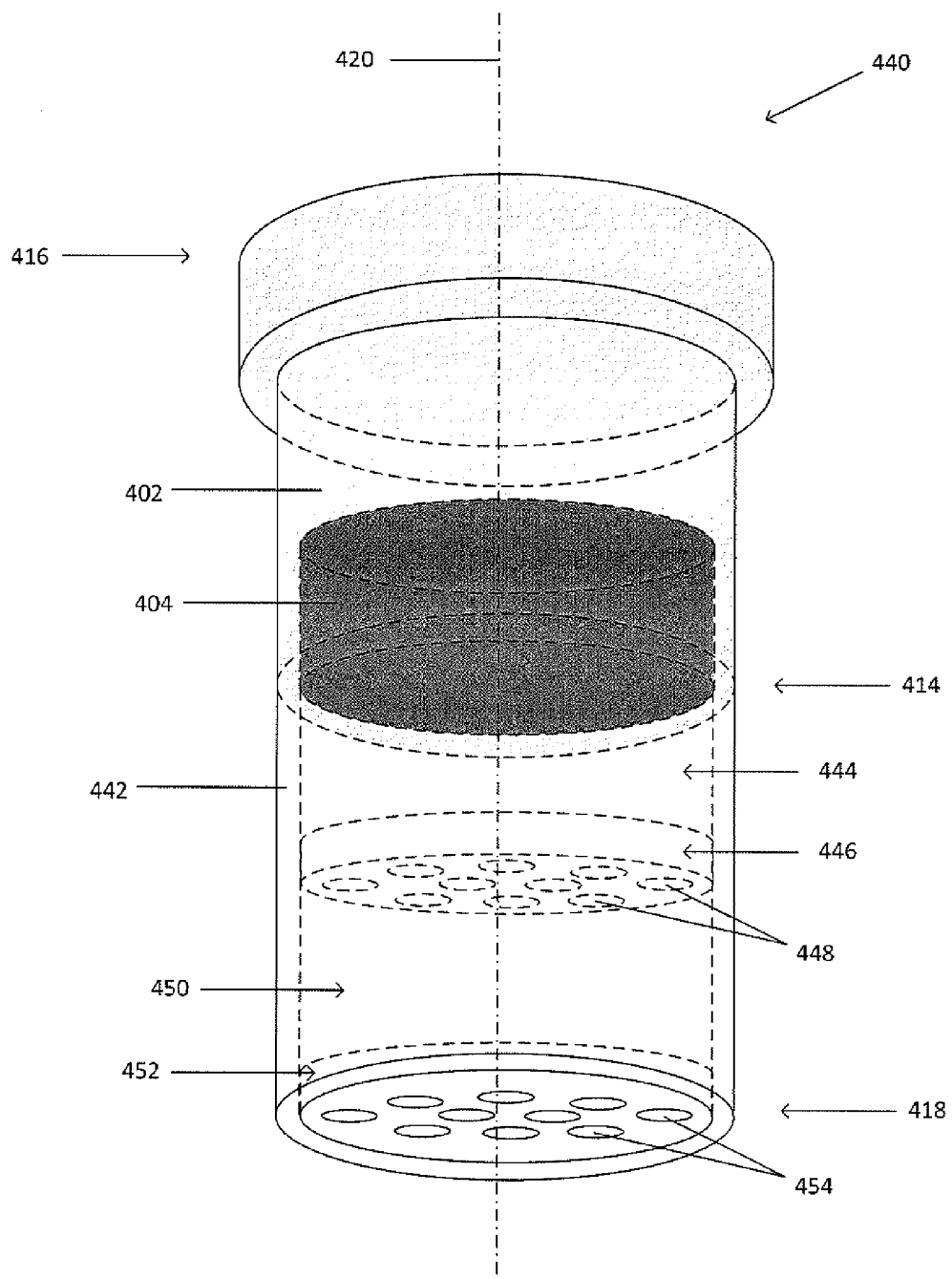

FIG. 4C shows an isometric view of a magnetic cap 440. The magnetic cap 440 is similar to the magnetic cap 400, except the magnetic cap 440 includes more than one filter 446 and 452. The filters 446 and 452 may be stacked successively (i.e. touching) or may be separated—thereby forming a repository 450 between the filters 446 and 452 and a fluid compartment 444 between the bottom end 414 of the stopper 402 and the uppermost filter 446. The fluid compartment 444 and the repository 450 may collect different analytes based on the size of the pores 448 and 454 in the filters 446 and 452, respectively.

The magnet may be, but is not limited to, a ring magnet, a bar magnet, a horseshoe magnet, a spherical magnet, a polygon-shaped magnet, a polyhedral-shaped magnet, a wand magnet, a kidney-shaped magnet, a trapezoidal magnet, a disk magnet, a cow magnet, a block or brick magnet, an electromagnet, and a switchable magnet.

The magnet may be permanently embedded or removably embedded within the stopper.

Magnetic Cap and Vessel System

The magnetic cap may be used in a system for separating a suspension suspected of containing a target analyte, the system including a vessel, the magnetic cap, and a primary fluid. The vessel is configured to hold a fluid, a suspension, a solution, or the like. Suppose, for example, the suspension includes three fractions. During centrifugation, the suspension may be divided into and settle into the three fractions, including a high density fraction, a medium density fraction, and a low density fraction. The primary fluid is a liquid substance that has a greater density than the density of the medium density fraction, though the primary fluid may have a density greater than the high density fraction. The primary fluid moves below the medium density fraction, thereby moving the medium density fraction upwards within the vessel. The system may also include a separating fluid, the separating fluid being a liquid substance that has a density that is less than the density the medium density fraction. The separating fluid inhibits non-target analytes from passing through towards the magnetic cap. The weak magnetic attraction may not overcome the force required to drag the non-target analytes through the separating fluid. However, the target analyte, which may be bound to particles attracted to the magnetic cap by stronger, more specific interactions, by, for example, a strong non-covalent interaction between complementary molecules, such as biotin and streptavidin, is capable of passing through the separating fluid. For example, the surface tension may break the weak bonds between the non-target analyte and the particle; or, the viscosity of the separating fluid may be great to inhibit passage of the weakly-bound non-target analyte. A plurality of primary fluids may also be used. The plurality of primary fluids may be used, for example, such that multiple density layers are formed or whereby each primary fluid is used sequentially to separate a suspension fraction, draw the target analytes out of the fraction, remove the separated suspension fraction, and repeat to withdraw individual target analytes from individual suspension layers.

The compositions of the primary fluid and the separating fluid may be selected so that suspension fractions and suspension fluid are immiscible in and inert with respect to the primary fluid and the separating fluid. Because the primary fluid and the separating fluid are immiscible in the suspension fractions and suspension fluid, the primary fluid and the separating fluid do not mix with the suspension fractions or the suspension fluid, which prevents a change in the density of the fluids and prevents a change in the density gradient within the layered suspension materials. Examples of suitable primary fluids include, but are not limited to, solution of colloidal silica particles coated with polyvinylpyrrolidone (e.g. Percoll), polysaccharide solution (e.g. Ficoll), iodixanol, cesium chloride, sucrose, sugar-based solutions, polymer-based solutions, surfactants, dextran, fluorinated liquids, such as perfluoroketones, perfluorocyclopentanone, perfluorocyclohexanone, fluorinated ketones, hydrofluoroethers, hydrofluorocarbons, perfluorocarbons, and perfluoropolyethers; silicon and silicon-based liquids, such as phenylmethyl siloxane.

Examples of suitable separating fluids include, but are not limited to, an organic solvent, a liquid wax, an oil, a gas, and combinations thereof; olive oil, mineral oil, silicone oil, chill-out liquid wax, paraffin wax, microcrystalline waxes, soy and palm waxes, candle waxes, thermoset waxes, hot melt adhesives, atactic polypropylene and polyolefin compounds, petroleum waxes, dental waxes, animal waxes, vegetable waxes, mineral waxes, petroleum waxes, and synthetic waxes, such as ethylenic polymers, chlorinated naphthalenes or hydrocarbon-type waxes; immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids.

Examples of suitable vessels include, but are not limited to, a tube, a well, a bottle, a flask, a beaker, a column, and a microfluidic device.

The system may also include a solution containing the particle to conjugate with the target analyte to form a target analyte-particle complex, such that when the magnetic cap is added to the vessel, the target analyte-particle complex is attracted to the magnetic cap.

Float and Tube System

The magnetic cap may be used in combination with a float and tube system. The primary fluid, the separating fluid, and the solution containing particles configured to bind to the target analyte may also be used in combination with the float and tube system. FIG. 5A shows an isometric view of an example tube and float system 500. The system 500 includes a tube 502 and a float 504 suspended within a suspension 506. In the example of FIG. 5A, the tube 502 has a circular cross-section, a first closed end 508, and a second open end 510. The open end 510 is sized to receive a sealing cap 512. The tube may also have two open ends that are sized to receive sealing caps, such as the example tube and float system 520 shown FIG. 5B. The system 520 is similar to the system 500 except the tube 502 is replaced by a tube 522 that includes two open ends 524 and 526 configured to receive the sealing cap 512 and a sealing cap 528, respectively. The tubes 502 and 522 have a generally cylindrical geometry, but may also have a tapered geometry that widens, narrows, or a combination thereof toward the open ends 510 and 524, respectively. Although the tubes 502 and 522 have a circular cross-section, in other embodiments, the tubes 502 and 522 can have elliptical, square, triangular, rectangular, octagonal, or any other suitable cross-sectional shape that substantially extends the length of the tube. The tubes 502 and 522 can be composed of a transparent or semitransparent flexible material, such as flexible plastic or another suitable material. The tube 502 may also include a plug 514, as seen in magnified view 516, at the closed end 508 to permit the removal of a fluid, the suspension, or a suspension fraction, whether with a syringe, a pump, by draining, or the like. The tube 502 may have a sidewall and a first diameter. The float 504 can be captured within the tube by an interference fit.

Figure 5C:
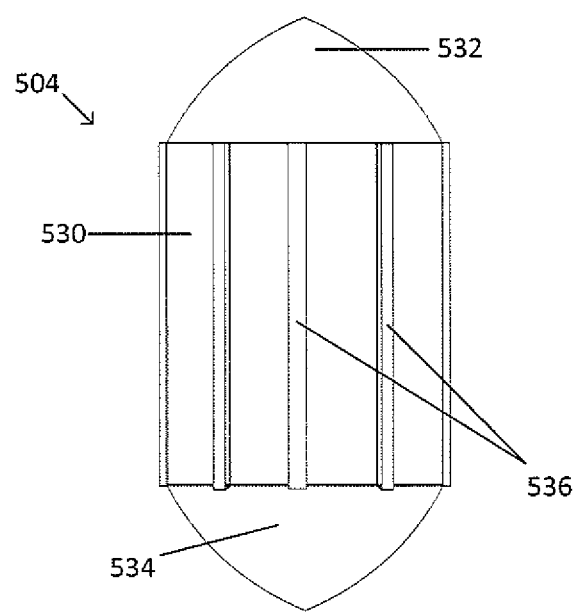
FIG. 5C shows an example float.

FIG. 5C shows an isometric view of the float 504 shown in FIGS. 5A and 5B. The float 504 includes a main body 530, two teardrop-shaped end caps 532 and 534, and support members 536 radially spaced and axially oriented on the main body 530. The float can also include two dome-shaped end caps or two cone-shaped end caps or any appropriately-shaped end cap. The support members 536 provide a support engagement with the inner wall of the tube 502. The support members 536 may extend the full length of the main body 530 or may extend a partial length of the main body 530, thereby providing an area on the main body 530 with no support member located at any circumferential point on the float 504. Alternatively, the support members 536 may be capable of being compressed by introducing an external force, such as by a clamp.

In alternative embodiments, the number of support members, support member spacing, and support member thickness can each be independently varied. The support members 536 can also be broken or segmented. The main body 530 is sized to have an outer diameter that is less than the inner diameter of the tube 502, thereby defining fluid retention channels between the outer surface of the main body 530 and the inner wall of the tube 502. The surfaces of the main body 530 between the support members 536 can be flat, curved or have another suitable geometry. In the example of FIG. 5C, the support members 536 and the main body 530 form a single structure. The support members 536 and the main body 530, alternatively, may be separate structures.

Embodiments include other types of geometric shapes for float end caps. The top end cap may be teardrop-shaped, dome-shaped, cone-shaped, or any other appropriate shape. The bottom end cap may be teardrop-shaped, dome-shaped, cone-shaped, or any other appropriate shape. In other embodiments, the main body of the float 504 can include a variety of different support structures for separating target materials, supporting the tube wall, or directing the suspension fluid around the float during centrifugation. Embodiments are not intended to be limited to these examples. The main body may include a number of protrusions that provide support for the tube. In alternative embodiments, the number and pattern of protrusions can be varied. The main body may include a single continuous helical structure or ridge that spirals around the main body creating a helical channel. In other embodiments, the helical ridge can be rounded or broken or segmented to allow fluid to flow between adjacent turns of the helical ridge. In various embodiments, the helical ridge spacing and rib thickness can be independently varied. In another embodiment, the main body may include a support member extending radially from and circumferentially around the main body. In another embodiment, the support members may be tapered.

The float can be composed of a variety of different materials including, but not limited to, metals; organic or inorganic materials; ferrous plastics; sintered metal; machined metal; plastic materials and combinations thereof.

The sealing cap may be composed of a variety of different materials including, but not limited to, organic or inorganic materials; plastic materials; and combination thereof.

The end caps of the float may be manufactured as a portion of the main body, thereby being one singular structure, by machining, injection molding, additive techniques, or the like; or, the end caps may be connected to the main body by a press fit, an adhesive, a screw, any other appropriate method by which to hold at least two pieces together, or combinations thereof.

The plug 514 may be composed of re-sealable rubber or other suitable re-sealable material that can be repeatedly punctured with a needle or other sharp implement to access contents of the tube 502 interior and re-seals when the needle or implement is removed. The plug 514 can be formed in the openings and/or the bottom interior of the tube using heated liquid rubber that can be shaped and hardens as the rubber cools. The adhesive used to attach the plug 514 to the wall of the opening and tube interior and can be a polymer-based adhesive, an epoxy, a contact adhesive or any other suitable material for bonding rubber to plastic or creating a thermal bond.

Methods

Figure 6A:
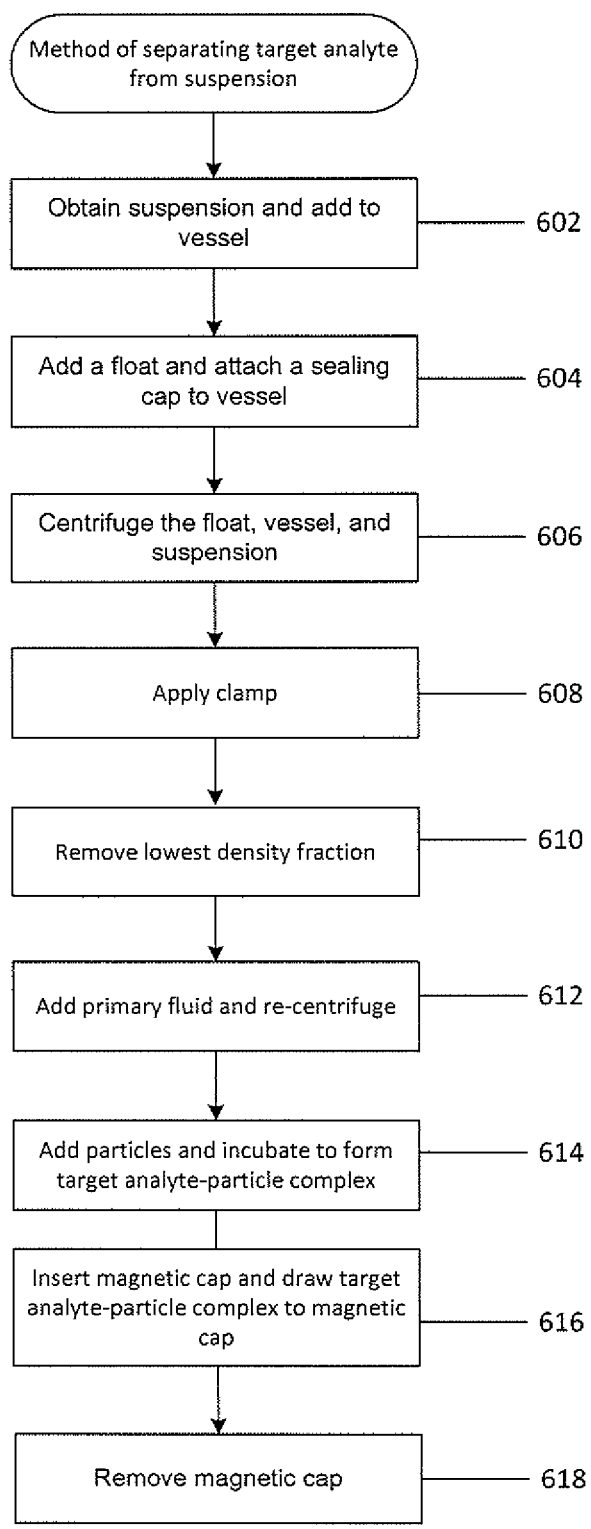
FIG. 6A shows a flowchart of an example method for separating a target analyte from a suspension.
Figure 6B:
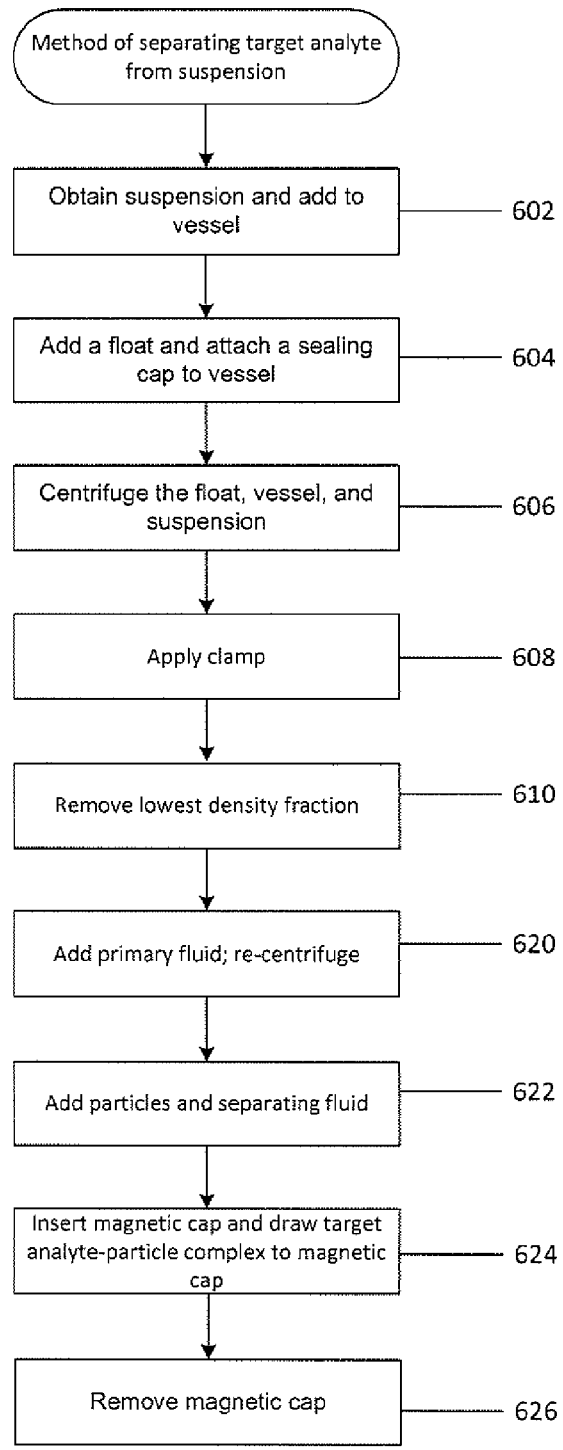
FIG. 6B shows a flowchart of an example method for separating a target analyte from a suspension.

FIGS. 6A and 6B show flow diagrams of example methods for separating a target analyte from a suspension. Referring now to FIG. 6A, in block 602, a suspension is obtained and then added to a vessel, such as a tube. In block 604, a float is added to the vessel and a sealing cap seals the vessel. FIG. 5A shows the suspension 506, such as blood, added to a vessel, such as the tube 502. The float 504 is then added to the tube 502 and the sealing cap 512 is added to the tube 502 to seal the opening 508. A sample suspension can be urine, blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target analyte can be a cell, such as ova or a circulating tumor cell ("CTC"), a circulating endothelial cell, a fetal cell, a nucleated red blood cell, a red blood cell, a vesicle, a liposome, a protein, a nucleic acid, a biological molecule, a naturally occurring or artificially prepared microscopic unit having an enclosed membrane, parasites, microorganisms, viruses, or inflammatory cells.

Returning to FIG. 6A, in block 606, the float, the tube, and the suspension undergo density-based separation, such as by centrifugation, thereby permitting separation of the suspension into density-based fractions along an axial position in the tube based on density. In block 608, a clamp is applied to the system.

FIG. 7A shows an isometric view of the tube and float system 500 having undergone density-based separation, such as by centrifugation. Suppose, for example, the suspension includes three fractions. The suspension separates into three fractions, with a highest density fraction 703 located on the bottom, a lowest density fraction 701 located on top, and a medium density fraction 702 located in between. The float 504 may have any appropriate density to settle within one of the fractions. The density of the float 504 can be selected so that the float 504 settles at the same axial position of the target analyte. The target analyte can be trapped within an analysis area between the float 504 and the tube 502.

After the suspension is separated into fractions 701-703, a seal may be formed between the tube 502 and the float 504. For example, as shown in FIG. 7A, a clamp 704 may be placed around the tube 502 at the interface between the medium density fraction 702 and the highest density fraction 703 to form the seal. The clamp 704 may be, but is not limited to, a compressible metal ring, a collet clamp, an O-ring, a pipe clamp, a hose clamp, a spring clamp, a strap clamp, a tie, such as a zip tie, or a piezoelectric ring. The clamp 704 may or may not include a thermal element, such as a heated wire, to soften the tube 502. The clamp 704 circumferentially applies pressure directed toward the central axis of the tube 502. The inward circumferential pressure causes the tube 502 to collapse inwardly. The clamp 704 forces the inner wall of the tube 502 against the main body 530 of the float 504 essentially forming a seal between the medium density fraction 702 and the highest density fraction 703, as shown in magnified cross-sectional view 706. The seal inhibits fluid flow between the medium density fraction 702 and the highest density fraction 703 and holds the float 504 in place against the buoyant forces exerted by the highest density fraction 703. Alternatively, the seal may be formed by ultrasonically welding the tube 502 to the float 504. Alternatively, the seal may be formed by melting the tube 502 to the float 504.

FIG. 7B shows a collet clamp 712 placed on the tube 502. Magnified view 718 shows a cross-sectional view across a system with the collet clamp 712. The collet clamp 712 is a clamp having an inner collar 716 and an outer collar 714, the outer collar 714 being capable of receiving the inner collar 716. The inner collar 716 may be segmented. The outer and inner collars 714 and 716 include complementary threads. The outer and inner collars 714 and 716 both include a cavity to receive the tube 502. The threads of the outer collar 714 engage the threads of the inner collar 716, and screwing the outer collar 714 further onto the inner collar 716 causes the inner collar 716 to compress. When the collet clamp 712 is placed around the tube 502 and the outer collar 714 is screwed onto the inner collar 716, the inner collar 716 compresses, thereby applying uniform pressure circumferentially on the tube to cause the tube to compress towards the float 504 and creating a seal.

Figure 8:
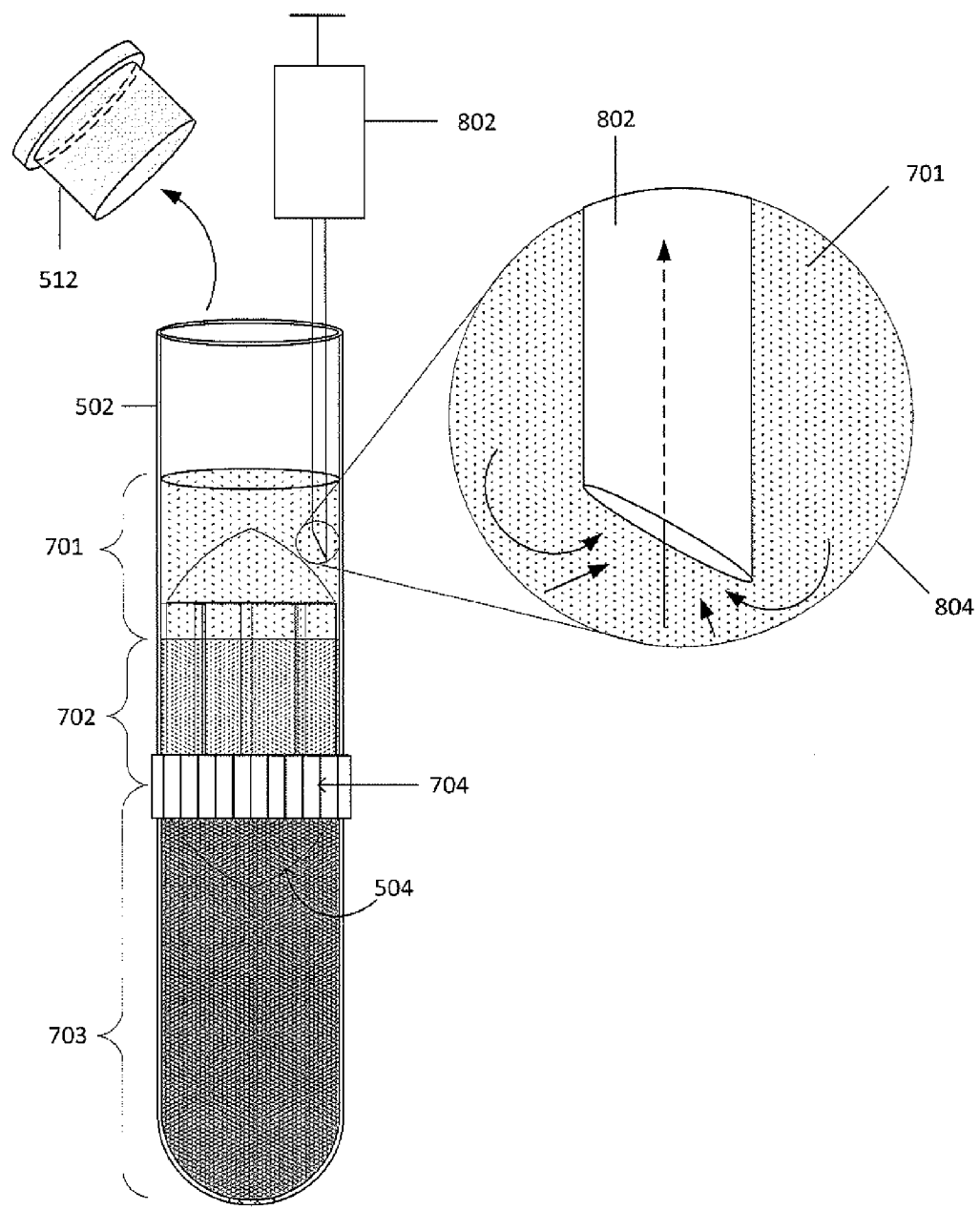
FIG. 8 shows a lowest density fraction being removed from an example vessel after a suspension has undergone density-based separation.

Returning to FIG. 6A, in block 610, the lowest density fraction is removed from the tube. FIG. 8 shows the lowest density fraction 701 being removed using an extraction device 802. The extraction device 802 may be a pump or syringe. With the clamp 704 in place, the lowest density fraction 701 can be removed by pouring off, pipetting, aspirating, or pumping. Alternatively, the lowest density fraction 701 may be removed prior to the clamp 704 clamping the tube 502.

Returning to FIG. 6A, in block 612, the primary fluid is added to the tube and the system is then re-centrifuged to wash the target analyte off of the tube and float surfaces and re-suspend the target analyte. In block 614, the solution including the particle to conjugate to the target analyte to form the target analyte-particle complex is added to the tube and incubated. In block 616, the magnetic cap is inserted and the target analyte-particle complex is drawn to the magnetic cap. In block 618, the magnetic cap is removed.

FIG. 9 shows the magnetic cap 100 inserted into the tube 502. The magnetic cap 100 may be inserted after a primary fluid 902 has been added to the tube 502, the system has been re-centrifuged, and a solution including a particle 910 to conjugate to the target analyte 908 to form a target analyte-particle complex 906 has been added. The primary fluid 902, having a density greater than the medium density fraction 702, causes the medium density fraction 702 to move upwards within the tube 502 after re-centrifugation. The seal formed by the clamp 704 prevents any fluids, including the highest density fraction 703, from moving past the clamp 704. The float 504 does not move further down in the tube 502 due to the clamp 704. The target analyte-particle complex 906 includes the target analyte 908 and the particle 910. The particle 910 is configured to be attracted to the magnetic field or magnetic gradient introduced by a magnet, such as the magnet 106 described above with reference to FIG. 1. The target analyte-particle complex 906 is then drawn to the magnet 106 of the magnetic cap 100. The target analyte-particle complex 906 is held to the sheath 124 and the magnetic cap 100 is then removed from the tube 502. The magnetic cap 100 may be inserted into a vessel including a solution, such as a buffer, and the magnetic insert 102 may then be removed from the receiving piece 116, thereby removing the target analyte-particle complex 906 from the sheath 124. The target analyte-particle complex 906 may then undergo further processing or testing.

Alternatively, the solution including the particle to conjugate to the target analyte to form the target analyte-particle complex may be added before re-centrifugation.

Before the target analyte-particle is attracted to the magnetic cap 100, magnets may be placed externally to the tube to draw the target analyte-particle complex to the sidewall of the tube. The external magnets may be placed on opposite sides of the tube 502 to draw the target analyte-complex 906 to the sidewall of the tube 502. Alternatively, a single magnet may be used to draw the target analyte-particle complex 906 to one side of the tube 502. Alternatively, a single donut- or ring-shaped magnet may encircle the tube 502 to draw the target analyte-particle complex 906 to the closest side of the tube 502. Alternatively, more than two magnets may be used to draw the target analyte-complex 906 to the closest side of the tube 502. The external magnets may be, but are not limited to, ring magnets, bar magnets, horseshoe magnets, spherical magnets, polygon-shaped magnets, polyhedral-shaped magnets, wand magnets, kidney-shaped magnets, trapezoidal magnets, disk magnets, cow magnets, block or brick magnets, electromagnets, and switchable magnets.

Referring now to FIG. 6B, blocks 602-610 refer to the same operations described above with reference to FIG. 6A. In block 620, the solution including the particle to conjugate to the target analyte to form the target analyte-particle complex is added to the tube and incubated. In block 622, the primary fluid and a separating fluid are added to the tube, and the system is then re-centrifuged. In block 624, the magnetic cap is inserted and the target analyte-particle complex is drawn to the magnetic cap. In block 626, the magnetic cap is removed from the tube.

Figure 10A:
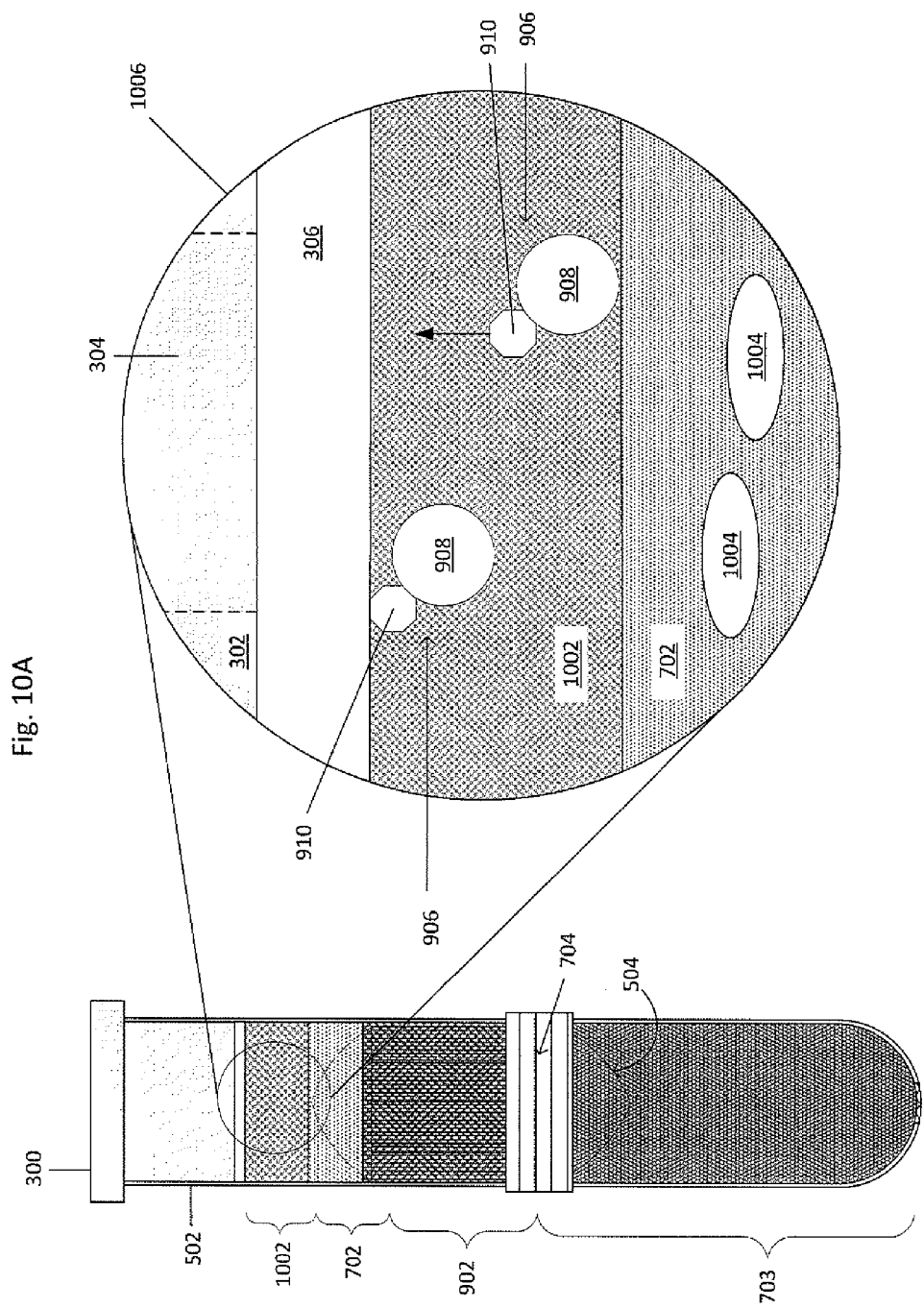
FIG. 10A shows an example system for separating a target analyte.

FIG. 10A shows the target analyte-particle complex 906 drawn to the magnetic cap 300 after the primary fluid 902 and a separating fluid 1002 are added to the tube 502 and after the system is re-centrifuged. The sealing cap 512 is removed from the tube 502 and the magnetic cap 300 is then inserted into the tube 502. The magnet 304 of the magnetic cap 300 creates a magnetic field or a magnetic gradient strong enough to draw the target analyte-complex 906 through the separating fluid 1002 to the analysis piece 306. Alternatively, an external magnet may be brought proximal to an outer wall of the tube 502 at a height substantially the same as the location of the medium density fraction 702 within the tube 502. The external magnet can be moved upwards towards the magnetic cap 300 and past the separating fluid 1012, which causes the target analyte-particle complex 906 move upward within the tube 502 towards the magnetic cap 300 as the external magnet moves upwards along the outside of the tube 502.

The primary fluid 902, having a density greater than the medium density fraction 702, displaces the medium density fraction 702, thereby causing the medium density fraction 702 to move upwards within the tube 502 after re-centrifugation. The separating fluid 1002, having a density less than the medium density fraction 702, sits on top of the medium density fraction 702. As shown in magnified view 1006, the separating fluid 1002 inhibits the non-target analytes 1004 from passing through the separating fluid 1002 and being held to the analysis piece 306, as the separating fluid 902 may break the weak bonds between the non-target analyte 1004 and the particle 910 so that the non-target analyte 1004 does not travel towards the cap magnet 304 and to the analysis piece 306. The weak magnetic attraction may not overcome the force required to drag the non-target analytes 1004 through the separating fluid 1002. However, the target analyte 908, which may be bound to the magnetic particles by stronger, more specific interactions, by, for example, a strong non-covalent interaction between complementary molecules, such as biotin and streptavidin, is capable of passing through the separating fluid 1002. The float 504 does not move further down in the tube 502 also due to the clamp 704. The seal formed by the clamp 704 prevents any fluids, including the highest density fraction 703, from moving passed the clamp 704 in any direction.

The magnetic cap 300 may then be removed from the tube 502. The analysis piece 306 may then be separated from the magnetic cap 300 and placed on or within an imaging device, such as a microscope, to analyze the target analyte; or, the analysis piece 306 may be further processed for subsequent analysis of the target analyte.

Figure 10B:
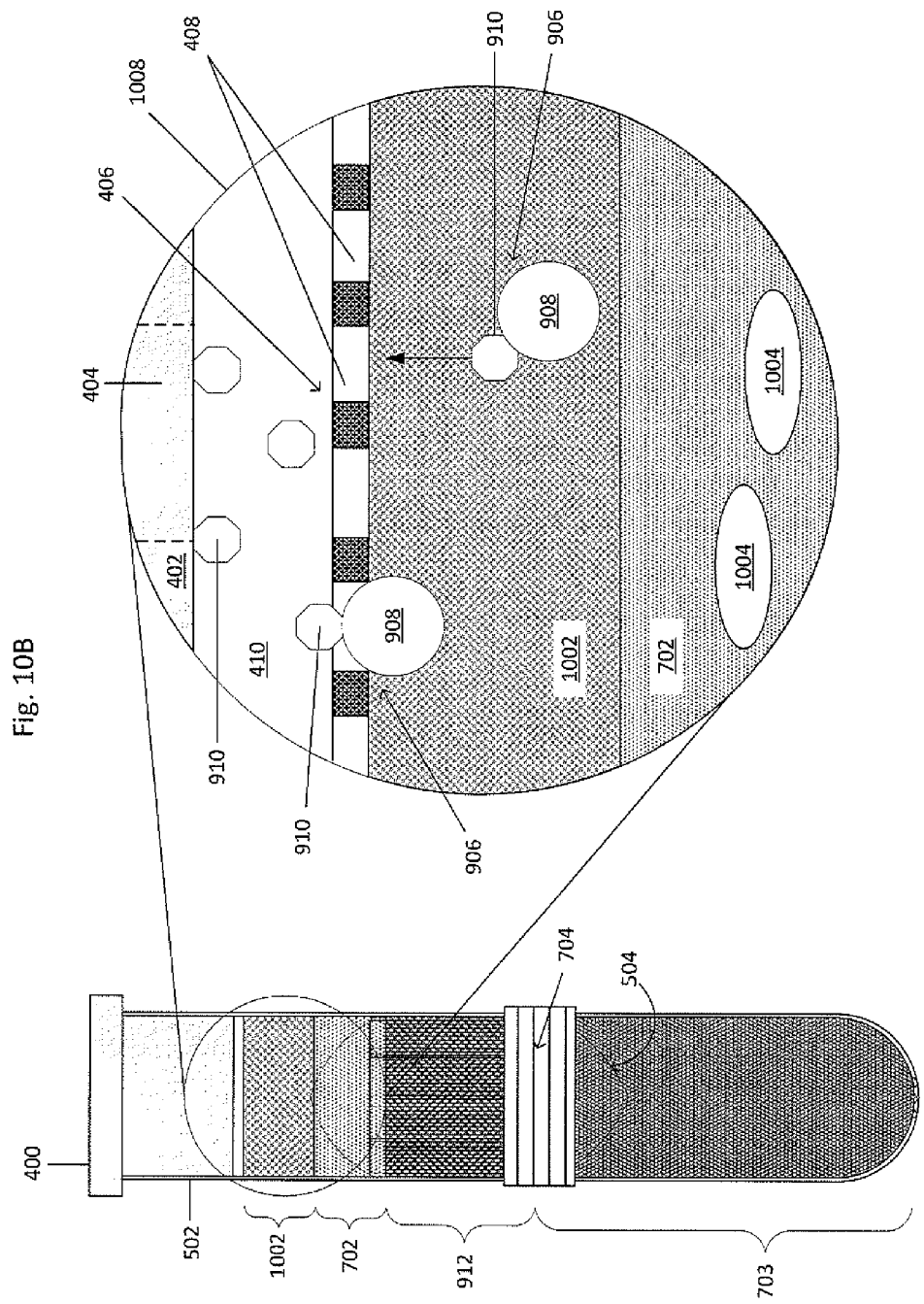
FIG. 10B shows an example system for separating a target analyte.

FIG. 10B shows the target analyte-particle complex 906 drawn to the magnetic cap 400 after the primary fluid 902 and a separating fluid 1002 are added to the tube 502 and after the system is re-centrifuged. The sealing cap 512 is removed from the tube 502 and the magnetic cap 400 described above with reference to FIG. 4 is then inserted into the tube 502. The magnet 404 of the magnetic cap 400 creates a magnetic field or a magnetic gradient that draws the target analyte-particle complex 906 through the separating fluid 1002 to the filter 406. The particle 910 may be unbound and therefore may pass through the pores 408 of the filter 406. The unbound particle 910 then collects in the fluid compartment 410 of the magnetic cap 400. The target analyte-particle complex 906 may then be trapped within or around the pore 408. Alternatively, an external magnet may be brought proximal to an outer wall of the tube 502 substantially the same as the location of the medium density fraction 702 within the tube 502. As the external magnet is moved upwards towards the magnetic cap 400 and passed the separating fluid 1002, moves upwards within the tube 502 towards the magnetic cap 400.

The primary fluid 902, having a density greater than the medium density fraction 702, displaces the medium density fraction 702, thereby causing the medium density fraction 702 to move upwards within the tube 502 after re-centrifugation. The separating fluid 1002, having a density less than the medium density fraction 702, sits on top of the medium density fraction 1002. As seen in magnified view 1008, the separating fluid 1002 inhibits the non-target analytes 1004 from passing through the separating fluid 1002 to the filter 406, as the separating fluid 1002 may break the weak bonds between the non-target analyte 1004 and the particle 910 so that the non-target analyte 1004 does not travel towards the cap magnet 404. The weak magnetic attraction may not overcome the force required to drag the non-target analytes 1004 through the separating fluid 1002. However, the target analyte 908, which may be bound to the magnetic particles by stronger, more specific interactions, by, for example, a strong non-covalent interaction between complementary molecules, such as biotin and streptavidin, is capable of passing through the separating fluid 1002. The float 504 does not move further down in the tube 502 also due to the clamp 704. The seal formed by the clamp 704 prevents any fluids, including the highest density fraction 703, from moving passed the clamp 704 in any direction.

The magnetic cap 400 may then be removed from the tube 502. The filter 406 may then be separated from the magnetic cap 400 and processed to remove the target analyte-particle complex 906; or, the target analyte-particle complex 906 may be flushed out of the pore 408.

After the magnetic cap has been removed, the magnetic cap may be washed to remove unwanted material or particles from the cap. The wash may occur by spraying or rinsing the cap with a wash solution. Alternatively, the wash may be performed by immersing the cap into a container having a wash solution. A magnetic particle may be cleaved from a target analyte during the washing step by proteolytic cleavage, pH variation, or salt concentration variation (i.e. increasing the salt concentration of the surrounding solution to disrupt the molecular interactions that hold the target analyte to the magnetic particle). The target analyte may also be processed directly on the magnetic cap.

Alternatively, a sealing ring may be used to maintain the seal between the tube and the float so that clamp may be removed. The sealing ring may be placed between the clamp and the tube, and then tightened, thereby causing the tube to constrict and form the seal with the float. The sealing ring remains tightened and in tension. Alternatively, no clamp may be required to apply a uniform circumferential force, such as with a sealing ring composed of a piezoelectric material. Applying an electric potential to the sealing ring produces a mechanical strain, thereby causing the sealing ring to tighten and constrict the tube to form the seal between the tube and the float.

A solution containing a fluorescent probe may be used to label the target analyte, thereby providing a fluorescent signal for identification and characterization. The solution containing the fluorescent probe may be added to the suspension before the suspension is added to the vessel, after the suspension is added to the vessel but before centrifugation, or after the suspension has undergone centrifugation. The fluorescent probe includes a fluorescent molecule bound to a ligand. The target analyte may have a number of different types of surface markers. Each type of surface marker is a molecule, such an antigen, capable of attaching a particular ligand, such as an antibody. As a result, ligands can be used to classify the target analyte and determine the specific type of target analytes present in the suspension by conjugating ligands that attach to particular surface markers with a particular fluorescent molecule. Examples of suitable fluorescent molecules include, but are not limited to, quantum dots; commercially available dyes, such as fluorescein, FITC ("fluorescein isothiocyanate"), R-phycoerythrin ("PE"), Texas Red, allophycocyanin, Cy5, Cy7, cascade blue, DAPI ("4',6-diamidino-2-phenylindole") and TRITC ("tetramethylrhodamine isothiocyanate"); combinations of dyes, such as CY5PE, CY7APC, and CY7PE; and synthesized molecules, such as self-assembling nucleic acid structures. Many solutions may be used, such that each solution includes a different type of fluorescent molecule bound to a different ligand.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A cap to be received by an open end of a vessel, the cap comprising:
   a stopper including a bottom end and a top end;
   a magnet embedded within the stopper; and
   an analysis piece removably attached to the bottom end of the stopper,
   wherein the analysis piece is a cover slip or a slide.

2. The cap of claim 1, wherein the bottom end is sized and shaped to fit within an opening of the vessel and wherein the top end is wider than the opening of the vessel.

3. The cap of claim 1, wherein the bottom end is angled.

4. The cap of claim 1, further comprising at least one port to permit fluids to be introduced to and removed from the vessel.

5. The cap of claim 1, wherein the magnet is removably embedded within the stopper.

6. The cap of claim 1, wherein the magnet is permanently embedded within the stopper.

7. The cap of claim 1, further comprising an extraction port to receive an extraction prong to eject the analysis piece from the bottom end, the extraction port extending at least partially through the stopper.

8. A cap to be received by an open end of a vessel, the cap comprising:
   a stopper including a bottom end and a top end;
   a magnet embedded within the stopper;
   a sidewall extending downwardly from the bottom end to form a filter end;
   at least one filter in the filter end; and
   a fluid compartment located between the at least one filter and the bottom end,
   the at least one filter including at least one pore.

9. The cap of claim 8, further comprising two or more filters, and wherein the fluid compartment is located between the bottom end of the stopper and the filter located closest to the bottom end of the stopper.

10. The cap of claim 9, wherein the two or more filters are stacked.

11. The cap of claim 9, wherein the two or more filters are separated to form a repository between consecutive filters.

12. A cap to be received by an open end of a vessel, the cap comprising:
    a stopper including a bottom end and a top end;
    a magnet embedded within the stopper; and
    an inlet port to permit fluids to be introduced to the vessel and an outlet port to permit fluids to be removed from the vessel.

13. A cap to be received by an open end of a vessel, the cap comprising:
    a magnetic insert, the magnetic insert comprising:
        a stopper including a bottom end and a top end; and,
        a magnet extending outwardly from the bottom end,
        wherein the bottom end is sized and shaped to fit within an opening of the vessel; and,
    a receiving piece, the receiving piece comprising:
        a receiving stopper including a bottom end and a top end; and,
        a sheath to receive the magnet, the sheath extending outwardly from the bottom end,
        the bottom end to fit within the opening of the vessel, the receiving stopper to receive the bottom end of the stopper of the magnetic insert.

14. The cap of claim 13, the receiving piece further comprising a first slide removably attached to a first side of the sheath.

15. The cap of claim 14, the receiving piece further comprising a second slide removably attached to a second side of the sheath, wherein the first and second sides are opposite each other.

16. The cap of claim 13, wherein the top end of the stopper and the top end of the receiving stopper are wider than the opening of the vessel.

17. The cap of claim 13, wherein the magnet is a permanent magnet or an electromagnet.

18. The cap of claim 13, wherein the magnetic insert further comprises at least one port and the receiving piece comprises at least one opening corresponding to the at least one port to permit fluids to be introduced to and removed from the vessel.

19. The cap of claim 13, the magnetic insert further comprising an inlet port to permit fluids to be introduced to the vessel and an outlet port to permit fluids to be removed from the vessel; and the receiving piece further comprising an inlet opening corresponding to the inlet port and an outlet opening corresponding to the outlet port.

20. The cap of claim 13, wherein the sheath is sized and shaped to fit flush against a sidewall of the vessel.

21. The cap of claim 13, wherein the sheath is hemispherical, triangular, or rectangular.

* * * * *